United States Patent [19]
McGarry

[11] Patent Number: 5,527,318
[45] Date of Patent: Jun. 18, 1996

[54] SURGICAL CLIP ADVANCING SYSTEM

[75] Inventor: Richard A. McGarry, Norwalk, Conn.

[73] Assignee: United States Surgical Corportion, Norwalk, Conn.

[21] Appl. No.: 368,928

[22] Filed: Jan. 5, 1995

Related U.S. Application Data

[63] Continuation of Ser. No. 125,519, Sep. 22, 1993, Pat. No. 5,383,881, which is a continuation of Ser. No. 939,029, Sep. 2, 1992, abandoned, which is a continuation of Ser. No. 794,492, Nov. 19, 1991, abandoned, which is a division of Ser. No. 530,652, May 30, 1990, Pat. No. 5,084,057, which is a continuation-in-part of Ser. No. 381,265, Jul. 18, 1989, Pat. No. 5,100,420, and a continuation-in-part of Ser. No. 479,375, Feb. 13, 1990, Pat. No. 5,129,885, which is a continuation-in-part of Ser. No. 278,705, Jul. 22, 1994, which is a continuation of Ser. No. 184,361, Jan. 19, 1994, abandoned, which is a continuation of Ser. No. 000,993, Jan. 6, 1993, abandoned, which is a continuation of Ser. No. 723,067, Jun. 28, 1991, Pat. No. 5,197,970, which is a continuation of Ser. No. 635,219, Dec. 27, 1990, Pat. No. 5,030,226, which is a continuation of Ser. No. 144,486, Jan. 15, 1988, abandoned.

[51] Int. Cl.$^6$ ..................................................... A61B 17/04
[52] U.S. Cl. ........................ 606/139; 227/19; 227/175.1; 606/143
[58] Field of Search ..................................... 606/139, 142, 606/143; 227/19, 175, 180

[56] References Cited

U.S. PATENT DOCUMENTS

| | | |
|---|---|---|
| 4,152,920 | 5/1979 | Green . |
| 4,166,466 | 9/1979 | Jarvik . |
| 4,226,242 | 10/1980 | Jarvik . |
| 4,228,895 | 10/1980 | Larkin . |
| 4,242,902 | 1/1981 | Green . |
| 4,246,903 | 1/1981 | Larkin . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,372,316 | 2/1983 | Blake, III et al. . |
| 4,412,539 | 11/1983 | Jarvik . |
| 4,425,915 | 1/1984 | Ivanov . |
| 4,430,997 | 2/1984 | DiGiovanni et al. . |
| 4,450,839 | 5/1984 | Transue . |
| 4,452,357 | 6/1984 | Klieman et al. . |
| 4,452,376 | 6/1984 | Klieman et al. . |
| 4,471,780 | 9/1984 | Menges et al. . |
| 4,492,232 | 1/1985 | Green . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,557,263 | 12/1985 | Green . |
| 4,562,839 | 1/1986 | Blake, III et al. . |
| 4,572,183 | 2/1986 | Juska . |
| 4,576,166 | 3/1986 | Montgomery et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,646,740 | 3/1987 | Peters et al. . |
| 4,662,373 | 5/1987 | Montgomery et al. . |
| 4,662,374 | 5/1987 | Blake, III . |
| 4,712,549 | 12/1987 | Peters et al. . |
| 4,850,355 | 7/1989 | Brooks et al. . |
| 4,944,443 | 7/1990 | Oddsen et al. . |
| 5,030,226 | 7/1991 | Green et al. . |
| 5,040,715 | 8/1991 | Green et al. . |
| 5,049,152 | 9/1991 | Simon et al. . |
| 5,084,057 | 1/1992 | Green et al. . |
| 5,100,418 | 3/1992 | Yoon et al. . |
| 5,100,420 | 3/1992 | Green et al. . |
| 5,129,885 | 7/1992 | Green et al. . |
| 5,197,970 | 3/1993 | Green et al. . |

FOREIGN PATENT DOCUMENTS

WO90/0376  4/1990  WIPO .

OTHER PUBLICATIONS

Jaroslav F. Hulka, M. D., Laparoscopic Sterilization with Spring Clips, Apr. 1985, pp. 1–28.
Information Booklet for Auto Suture* Premium Surgiclip™ Titanium Disposable Automatic Clip Appliers.

Primary Examiner—Gary Jackson

[57] ABSTRACT

A clip advancing system is provided which includes a pusher bar having a nose with two transverse members, each transverse member including a distally facing clip contacting surface and an angular cam surface proximal thereto.

7 Claims, 23 Drawing Sheets

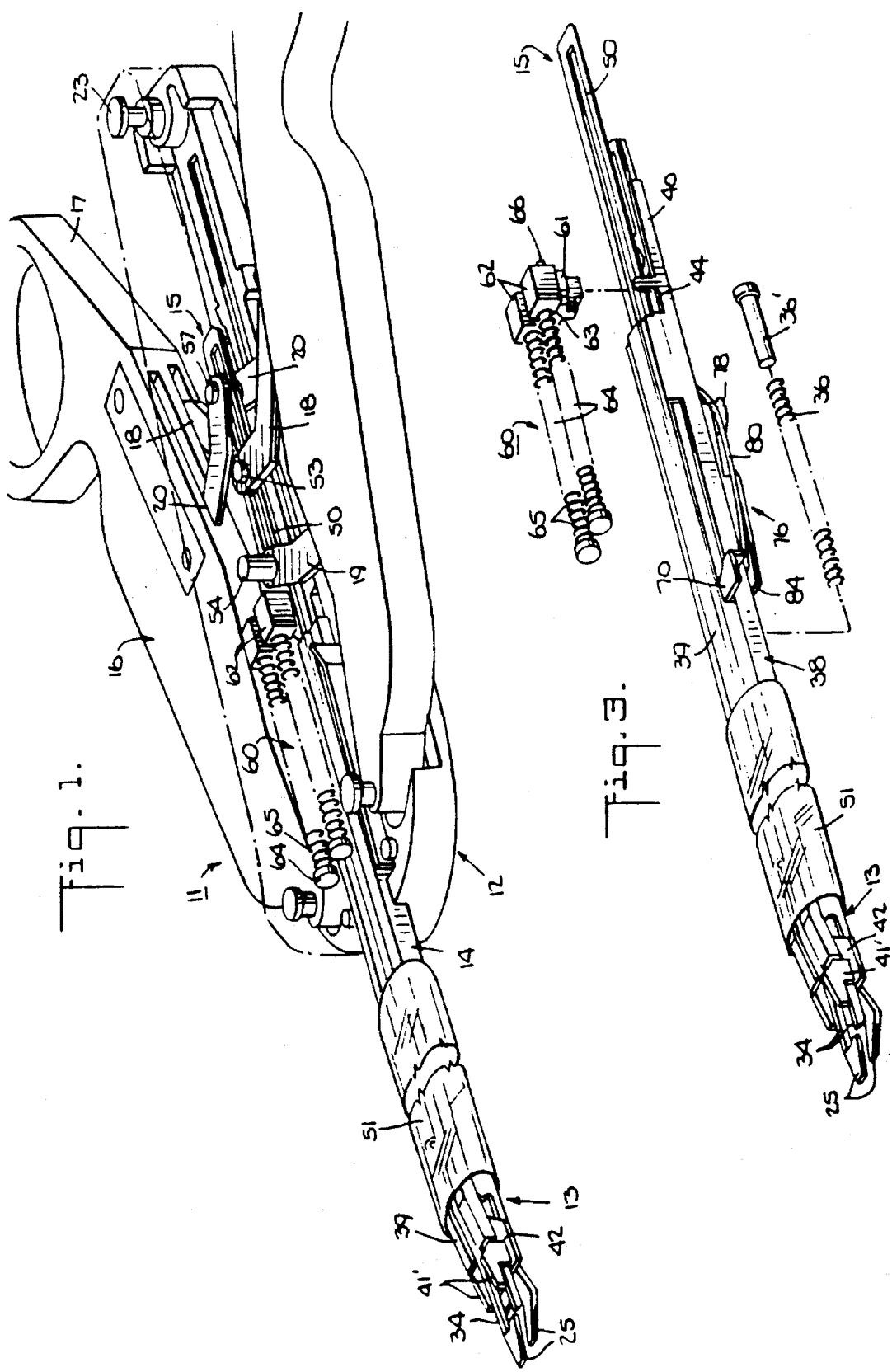

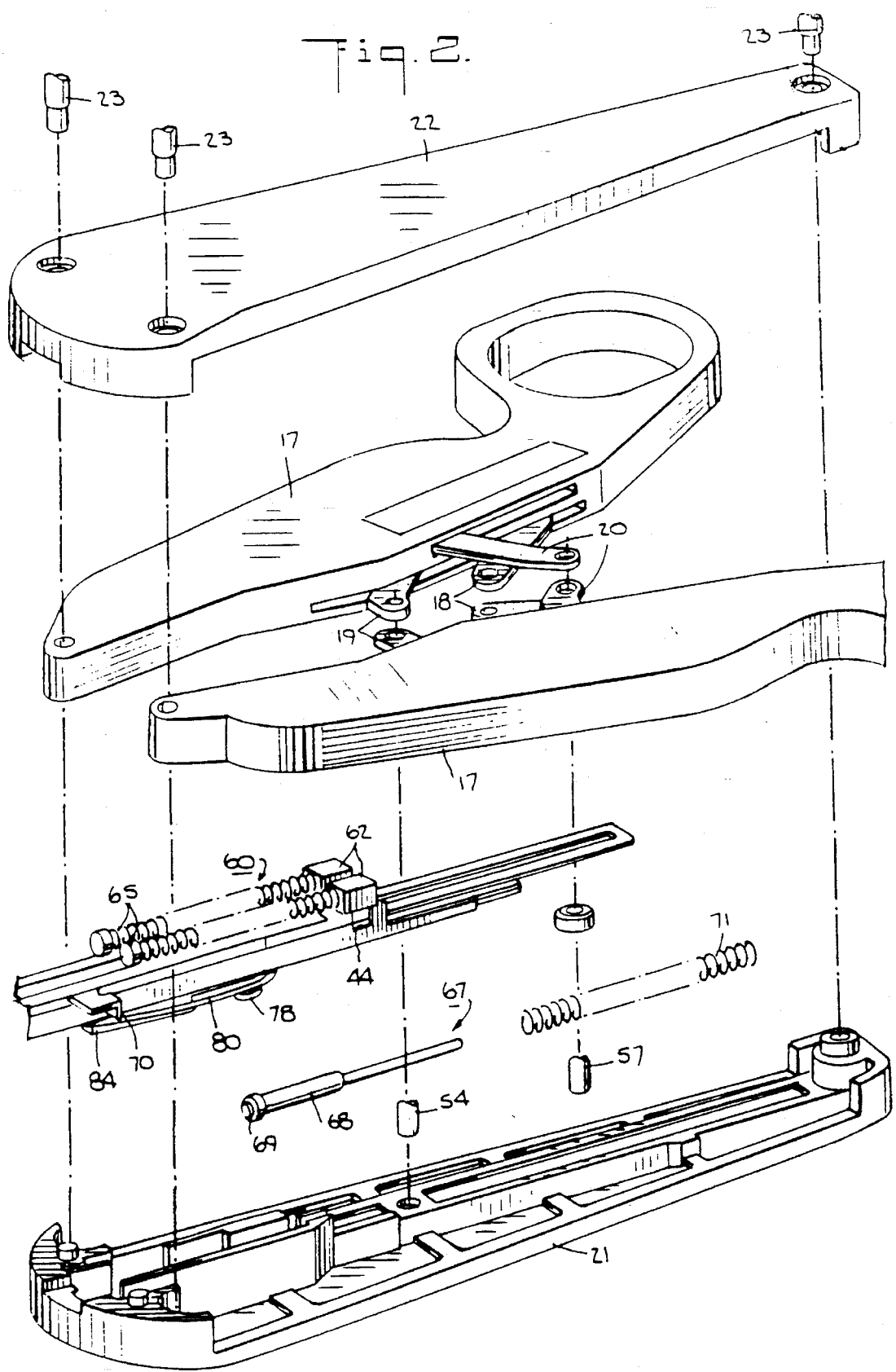

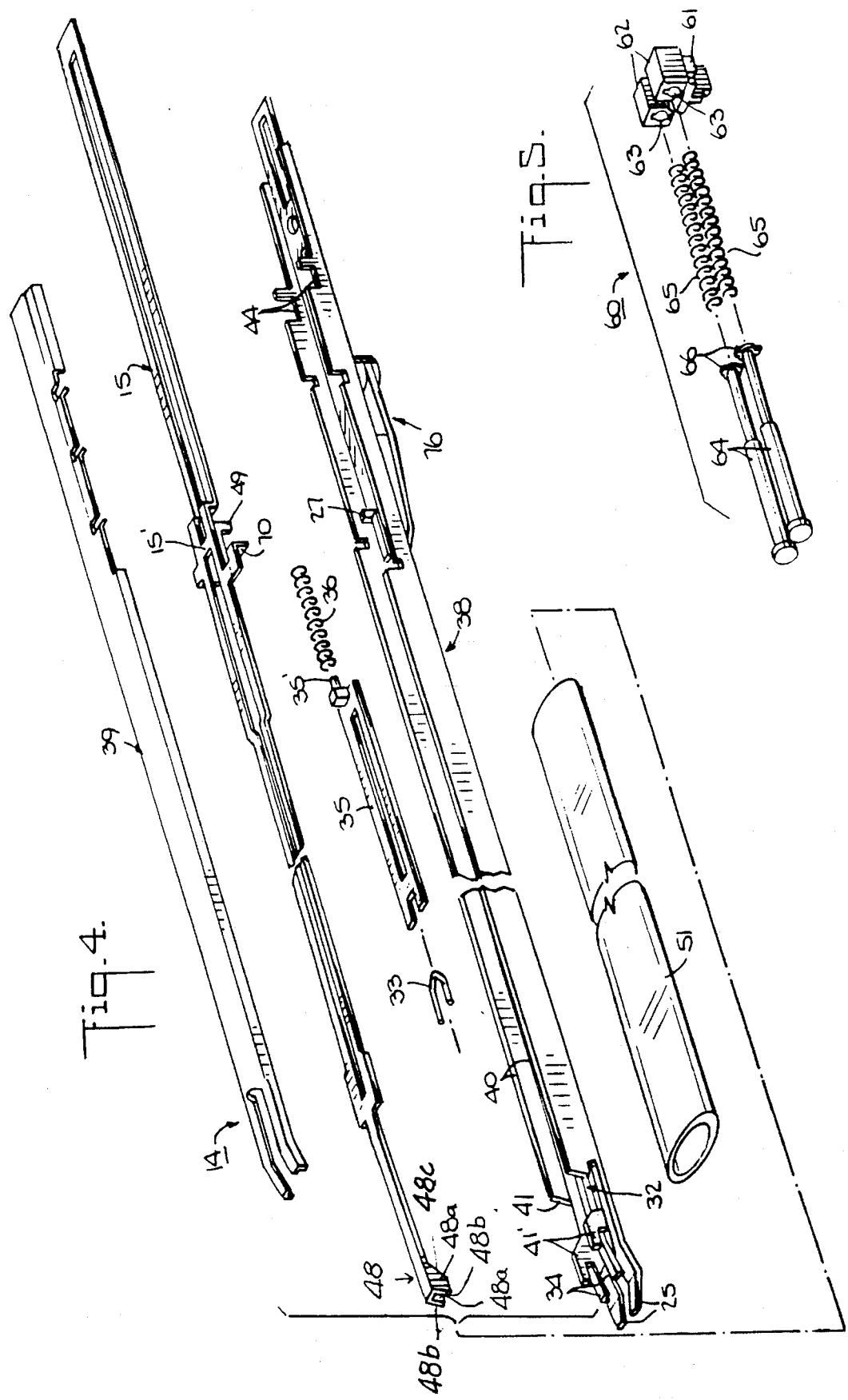

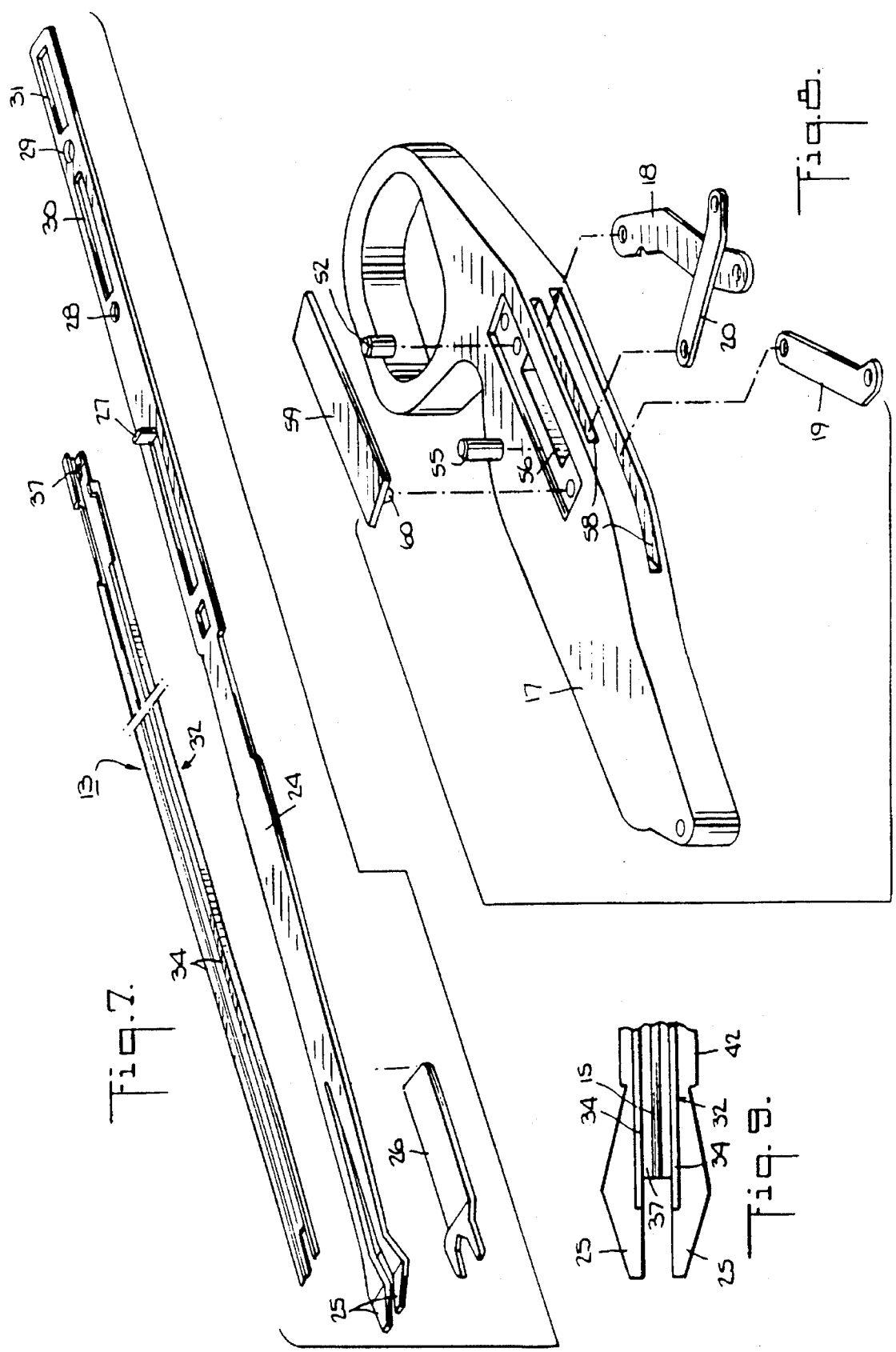

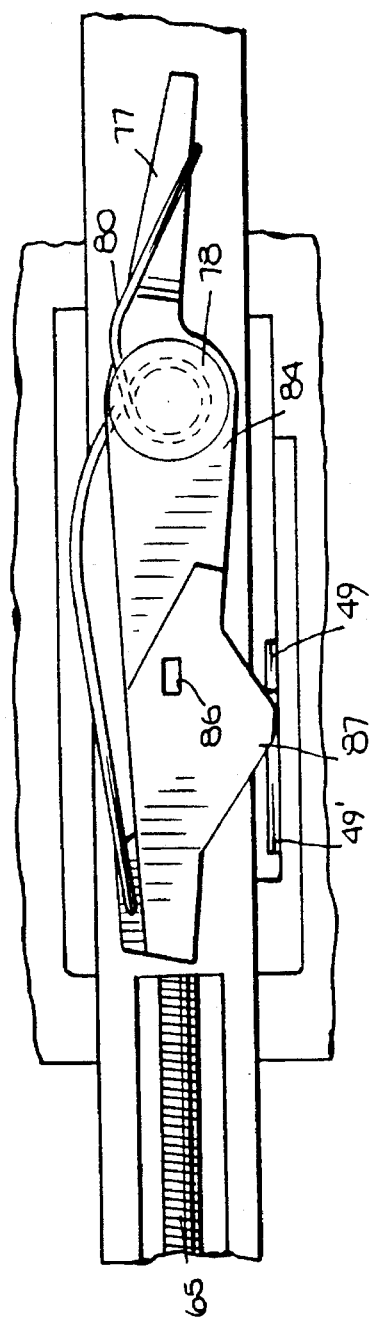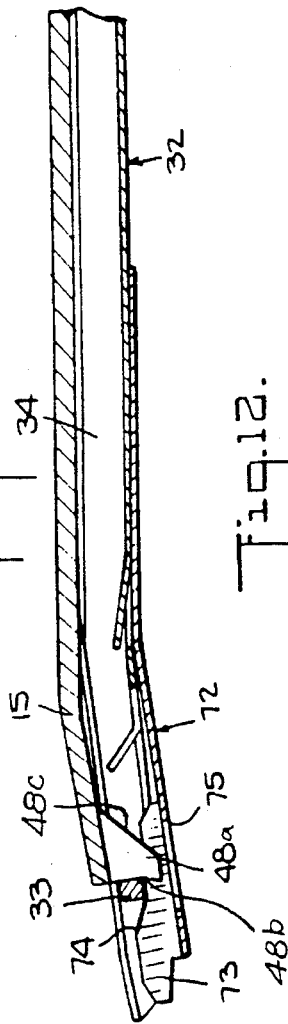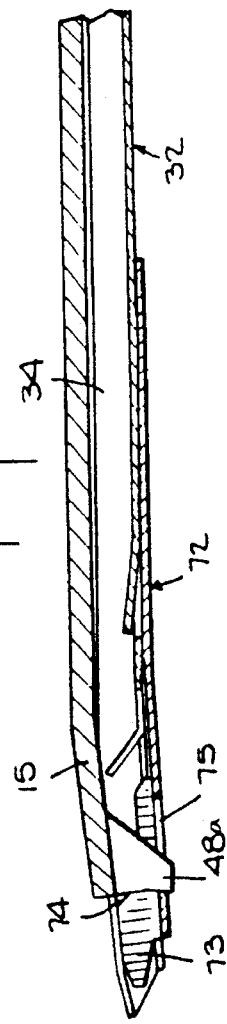

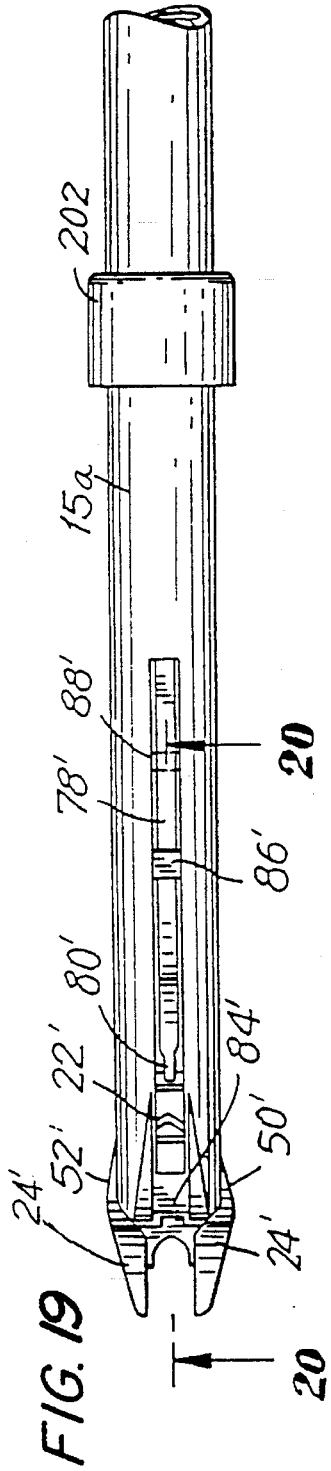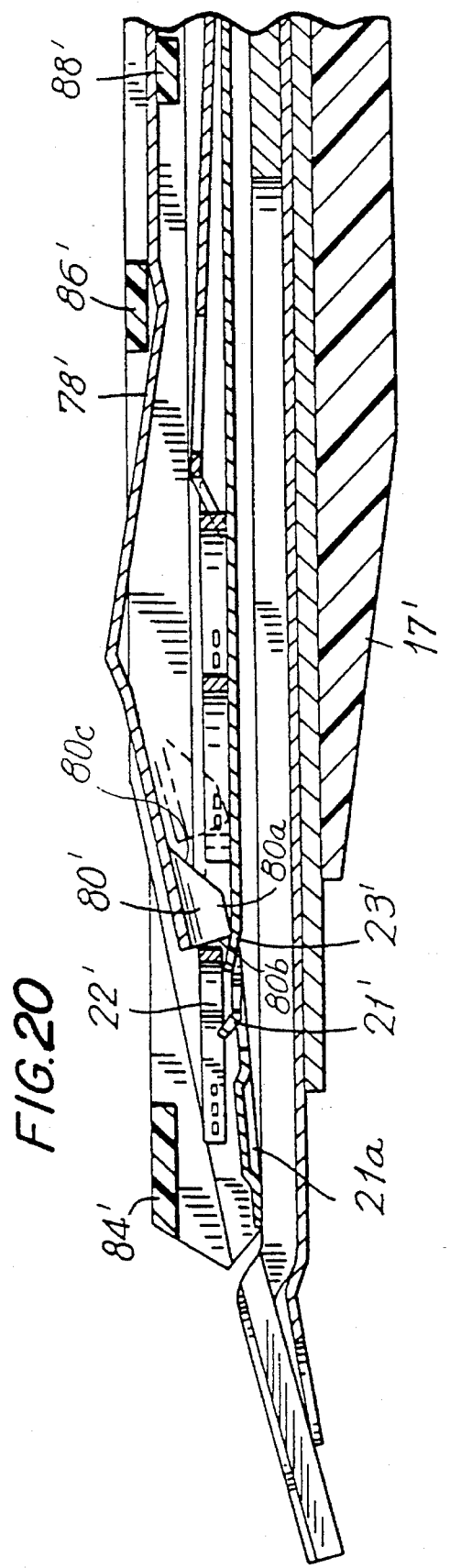
FIG.19
FIG.20

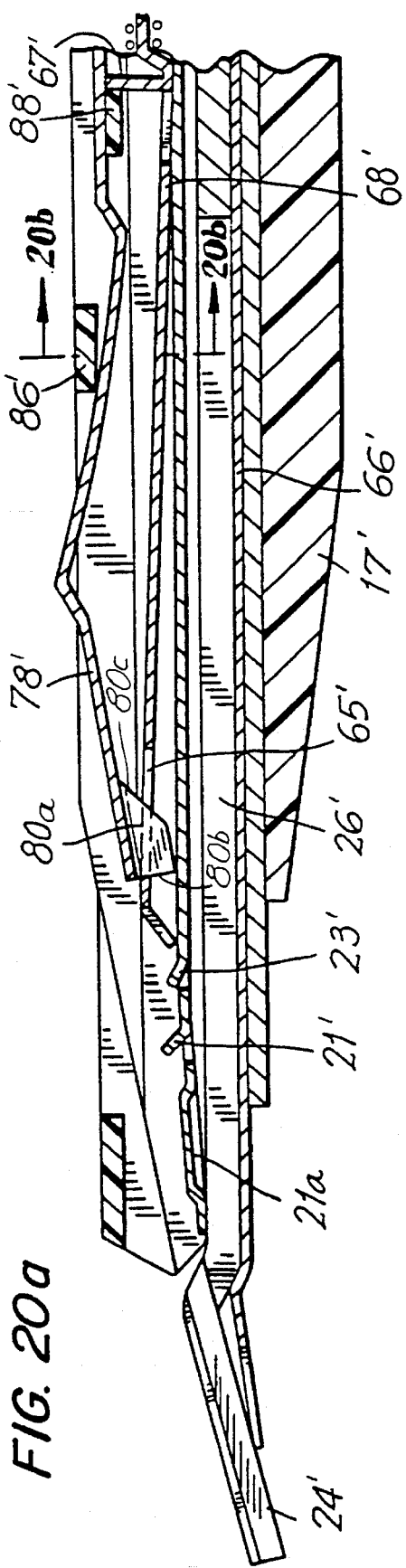
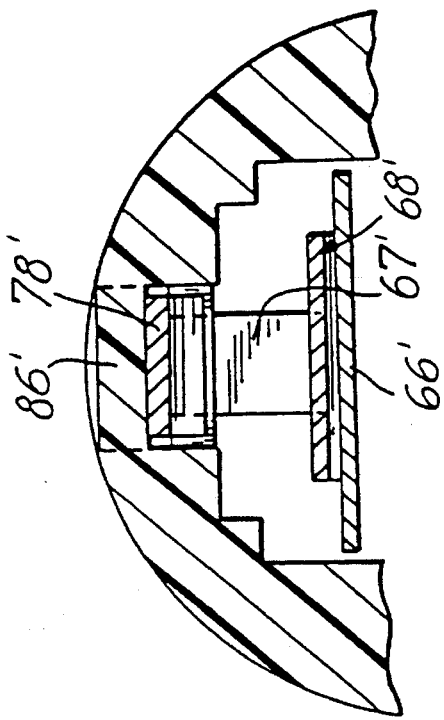
FIG. 20a
FIG. 20b

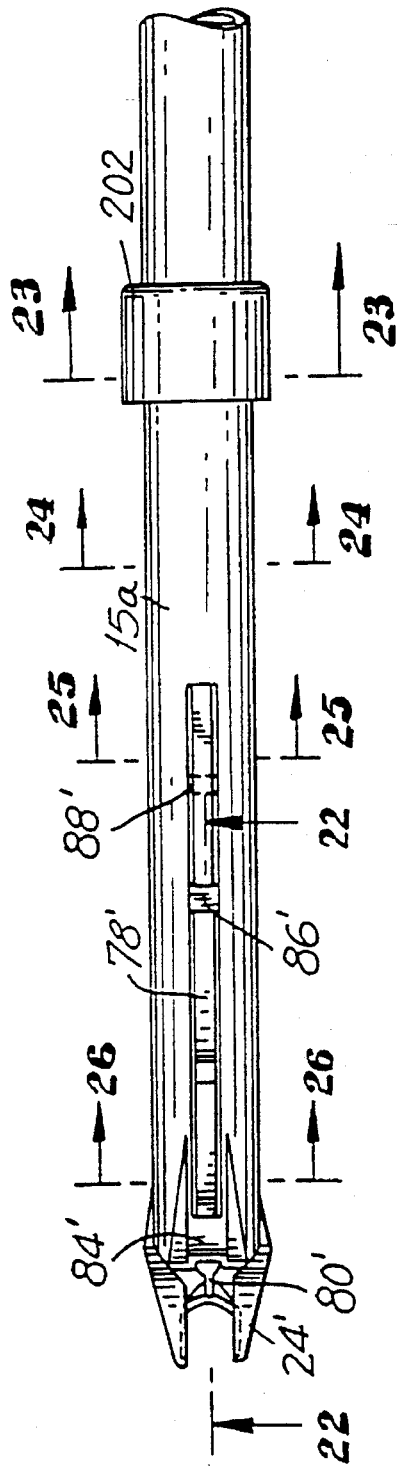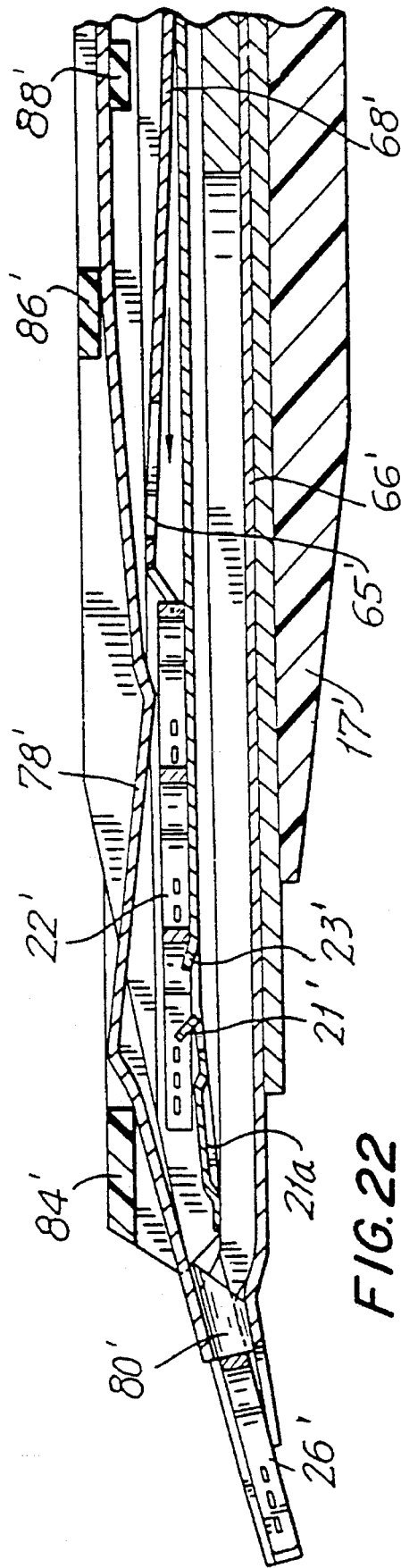

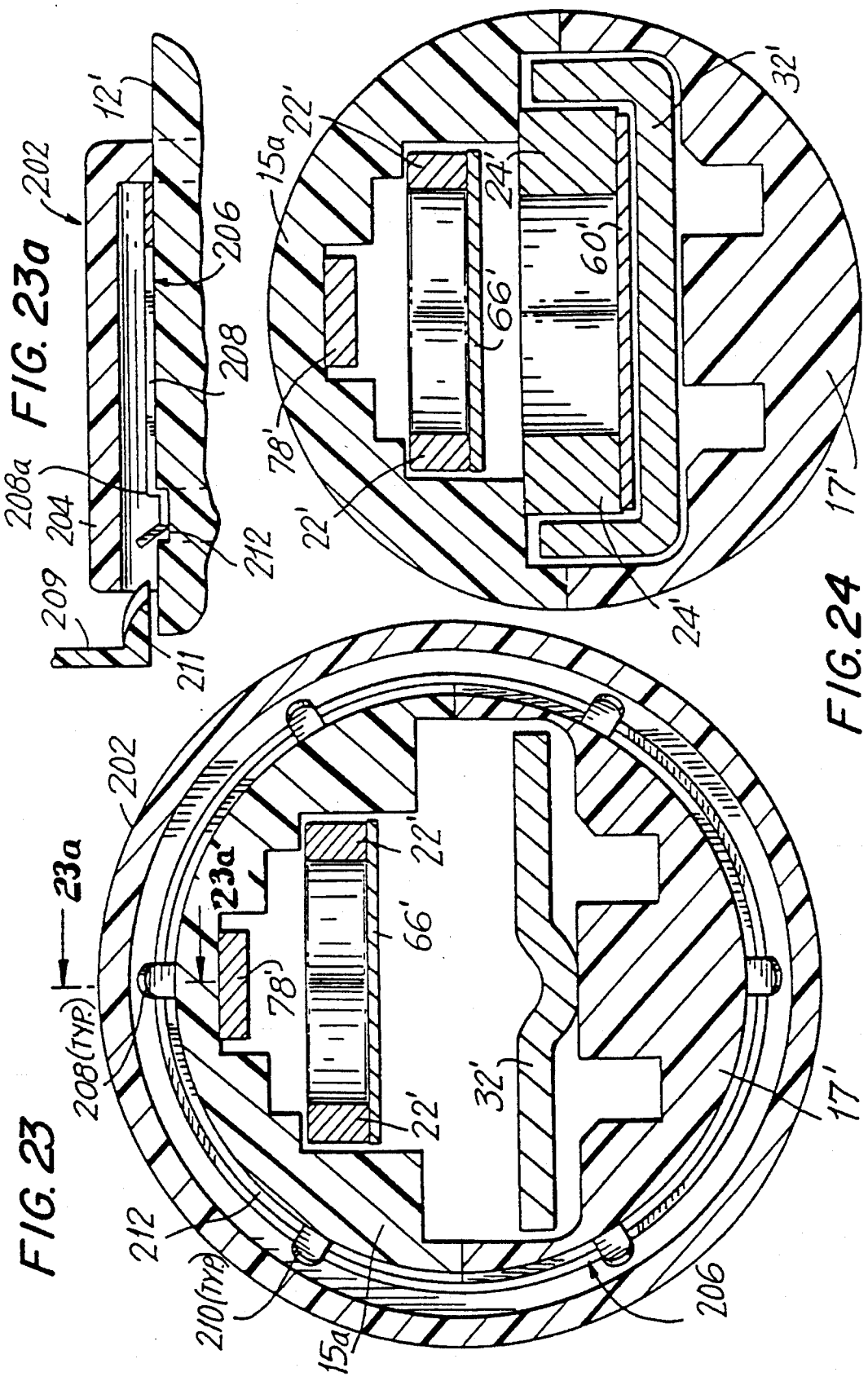

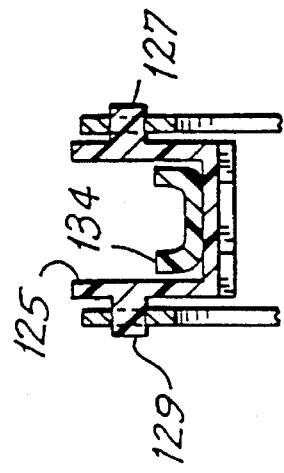
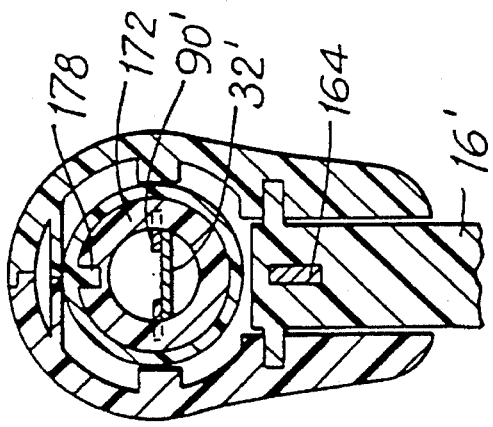
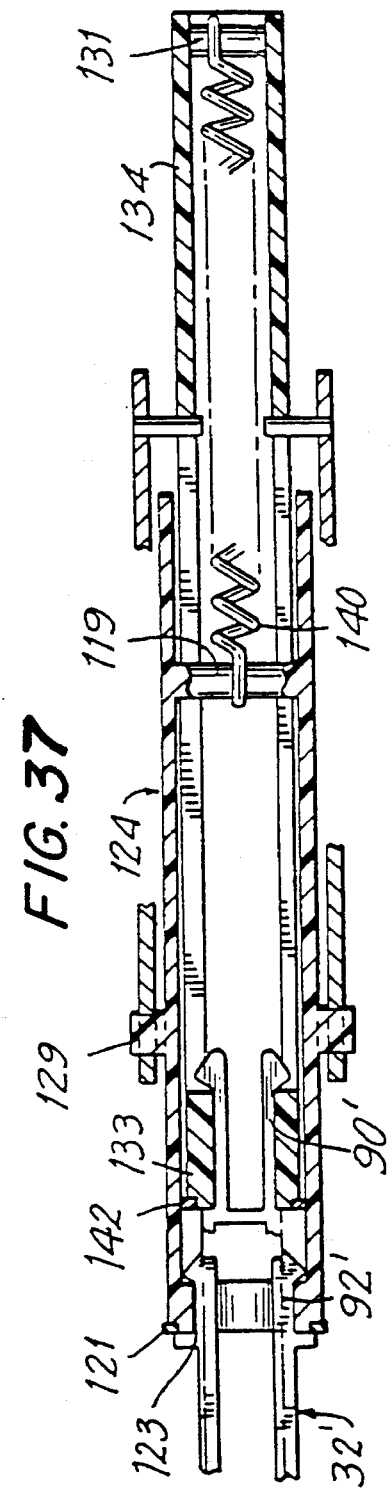

SURGICAL CLIP ADVANCING SYSTEM

CROSS-REFERENCE TO RELATED APPLICATIONS

This application is a continuation of Ser. No. 08/125,519, filed Sep. 22, 1993, now U.S. Pat. No. 5,383,881, which was a continuation of Ser. No. 07/939,029, filed Sep. 2, 1992, now abandoned, which was a continuation of Ser. No. 07/794,492, filed Nov. 19, 1991, now abandoned, which was a divisional of Ser. No. 07/530,652, filed May 30, 1990, now U.S. Pat. No. 5,084,057, which was a continuation-in-part of Ser. No. 07/381,265, filed Jul. 18, 1989, now U.S. Pat. No. 5,100,420, and a continuation-in-part of Ser. No. 07/479,375, filed Feb. 13, 1990, now U.S. Pat. No. 5,129,885. This application is also a continuation-in-part of co-pending Ser. No. 08/278,705, filed Jul. 22, 1994, which was a continuation of Ser. No. 08/184,361, filed Jan. 19, 1994, now abandoned, which was a continuation of Ser. No. 08/000,993, filed Jan. 6, 1993, now abandoned, which was a continuation of Ser. No. 07/723,067, filed Jun. 28, 1991, now U.S. Pat. No. 5,197,970, which was a continuation of Ser. No. 07/635,219, filed Dec. 27, 1990, now U.S. Pat. No. 5,030,226, which was a continuation of Ser. No. 07/144,486, filed Jan. 15, 1988, now abandoned.

BACKGROUND

1. Technical Field

This disclosure relates to a clip advancing system for a surgical clip applicator.

2. Description of Related Art

Heretofore, it has been known to use surgical clips, for example of metal, to provide hemostasis and occlude tissue structures in a wide variety of surgical procedures. To this end, use has been made of various applicators.

One approach has been to deliver a clip from a clip magazine to between a pair of jaws in response to the closing of a pair of handles by a surgeon with a subsequent crimping of the clip by the jaws via a continued closing of the handles together. However, such a pre-firing arrangement of a clip may pose problems to a surgeon. First, if the applicator has been completely discharged of clips, the surgeon may not be able to readily determine that the applicator is empty. Second, should an applicator be fired while about a vessel without a clip being discharged, the vessel may become damaged to such an extent that a clip cannot be subsequently applied at that location of the vessel. Third, the surgeon may not be able to see a clip being positioned between the jaws during closing of the handles to ensure proper position on a vessel.

U.S. Pat. Nos. 4,616,650 and 4,624,254, both of which are hereby incorporated by reference, disclose a surgical clip applying apparatus having a pair of ring-like handles. The handles are squeezed to force jaws to move distally relative to the apparatus where they are forced together by a pair of inclined surfaces. A surgical clip between the jaws is thereby squeezed closed.

In laparoscopic procedures surgery is performed in the interior of the abdomen through a small incision and/or guide sleeve; more generally, in endoscopic procedures surgery is performed in any hollow viscus of the body, e.g., through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that any instruments to be used in such procedures be both long and narrow.

Because endoscopic procedures are more common than laparoscopic procedures, to the extent the present disclosure contemplates endoscopic and/or laparoscopic procedures and apparatus, the disclosure shall speak in terms of endoscopic procedures and apparatus. However, use herein of terms such as "endoscopic", "endoscopically" and "endoscopic portion", among others, refer generally to instruments having elongated and relatively narrow operating portions for inserting into a cannula or a small wound in the skin and should not be construed to limit the present disclosure to an apparatus for applying surgical clips only in conjunction with an endoscopic tube. To the contrary, it is believed that "endoscopic" apparatus set forth in the present disclosure may find use in any procedure where access is limited to a small incision, including, but not limited to, laparoscopic procedures.

SUMMARY

Apparatus are disclosed herein which include advantageous clip advancing systems. An exemplary clip advancing system includes an elongated clip carrier defining a longitudinal axis, the clip carrier also defining a clip-supporting face. A plurality of surgical clips are in contact with the clip-supporting face of the elongated carrier. An elongated pusher bar is movably mounted with respect to the elongated clip carrier, the pusher bar having a distal end and a proximal end and including a nose at its distal end. The nose has a pair of members which extend substantially transverse to the longitudinal axis, each substantially transverse member including a distally facing clip contacting surface and an angular cam surface proximal to the clip contacting surface.

The advantageous clip advancing system(s) disclosed herein are adapted to function as part of a clip applying apparatus. The overall apparatus includes additional structures which cooperate to facilitate clip advancement and clip closure. For example, the advantageous clip advancing system(s) disclosed herein may function as part of an apparatus which includes a pair of flexible opposing jaws and a distally moving cam channel which cooperate to close surgical clips one at a time. The apparatus may also include a handle mechanism operatively connected to the pusher bar. The handle mechanism may be in the form of a pair of handles and one or more linkages for translating manually effectuated movement of the handles into longitudinal movement of the pusher bar relative to the elongated clip carrier.

In operation, the surgeon receives the advantageous clip advancing system as part of clip applying apparatus. Each time the surgeon desires to advance a clip from among the plurality of surgical clips, such clip would be contacted by the clip contacting surface of the pusher bar's nose and advanced through movement of the pusher bar with respect to the elongated clip carrier. Repositioning of the nose of the pusher bar behind the next available clip for subsequent advance of such next clip is facilitated by the proximal cam surfaces on the pusher bar's nose.

Many additional details concerning preferred clip applying apparatus which may benefit from the clip advancing system described herein are described below. For example, details as to a preferred locking mechanism for ensuring that the jaws of a surgical clip applying apparatus are not closed in the absence of a clip, details as to preferred endoscopic clip appliers, etc., are disclosed below. While these detailed disclosures provide useful information in appreciating the systems with which the unique clip advancing system may be used, these detailed disclosures are not intended and do not limit the scope of the claimed clip advancing system presented at the end of the present disclosure.

BRIEF DESCRIPTION OF THE DRAWINGS

Various embodiments are described herein with reference to the drawings, wherein:

FIG. 1 illustrates a part perspective view of a surgical clip applicator;

FIG. 2 illustrates a partial exploded view of the applicator of FIG. 1;

FIG. 3 illustrates a perspective view of a jaw blade assembly and channel assembly of the applicator;

FIG. 4 illustrates an exploded view of the jaw blade assembly and channel assembly;

FIG. 5 illustrates a spring assembly for biasing the channel assembly in a proximal direction;

FIG. 7 illustrates an exploded view of the clip carrier and jaw blade;

FIG. 8 illustrates a part perspective view of one handle and articulated linkage therefor; and FIG. 9 illustrates a partial plan view of the distal end of the applicator of FIG. 1;

FIG. 10 illustrates a bottom view of a locking mechanism;

FIG. 11 illustrates a cross sectional view of a retaining mechanism with a clip being discharged from a clip carrier;

FIG. 12 illustrates a view similar to FIG. 11 in the absence of a clip;

FIG. 19 is a plan view from above of the distal portion of the endoscopic section of the apparatus of FIG. 16;

FIG. 20 is a cross-sectional view taken along lines 20—20 of FIG. 19 illustrating the clip pusher in position to push the clip next in line to a position between the jaws of the apparatus;

FIG. 20a is a cross-sectional view of the distal portion of the endoscopic section of the apparatus of FIG. 16, illustrating the position of the clip pusher after the last clip has been advanced into the jaws of the endoscopic section;

FIG. 20b is a cross-sectional view taken along lines 20b—20b of FIG. 20a;

FIG. 21 is a plan view from above similar to FIG. 19 of the distal portion of the endoscopic section of the apparatus with the clip pusher in the distal position with the clip shown in FIG. 20 now positioned between the jaws;

FIG. 22 is a cross-sectional view taken along lines 22—22 of FIG. 21;

FIG. 23 is a cross-sectional view taken along lines 23—23 of FIG. 21, illustrating a safety locking feature;

FIG. 23a is a partial cross-sectional view of the safety locking feature of FIG. 23, taken along lines 23a—23a of FIG. 23;

FIG. 24 is a cross-sectional view taken along lines 24—24 of FIG. 21;

FIG. 35 is a cross-sectional view taken along lines 35—35 of FIG. 32 and illustrating the channel tube and pusher bar;

FIG. 36 is a view taken along lines 36—36 of FIG. 32 illustrating the pusher tube and the channel tube in cross-section;

FIG. 37 is a cross-sectional view taken along lines 37—37 of FIG. 32 illustrating the pusher tube mainspring and the connection between the pusher tube and the pusher bar;

DETAILED DESCRIPTION OF PREFERRED EMBODIMENT(S)

Figure 6:
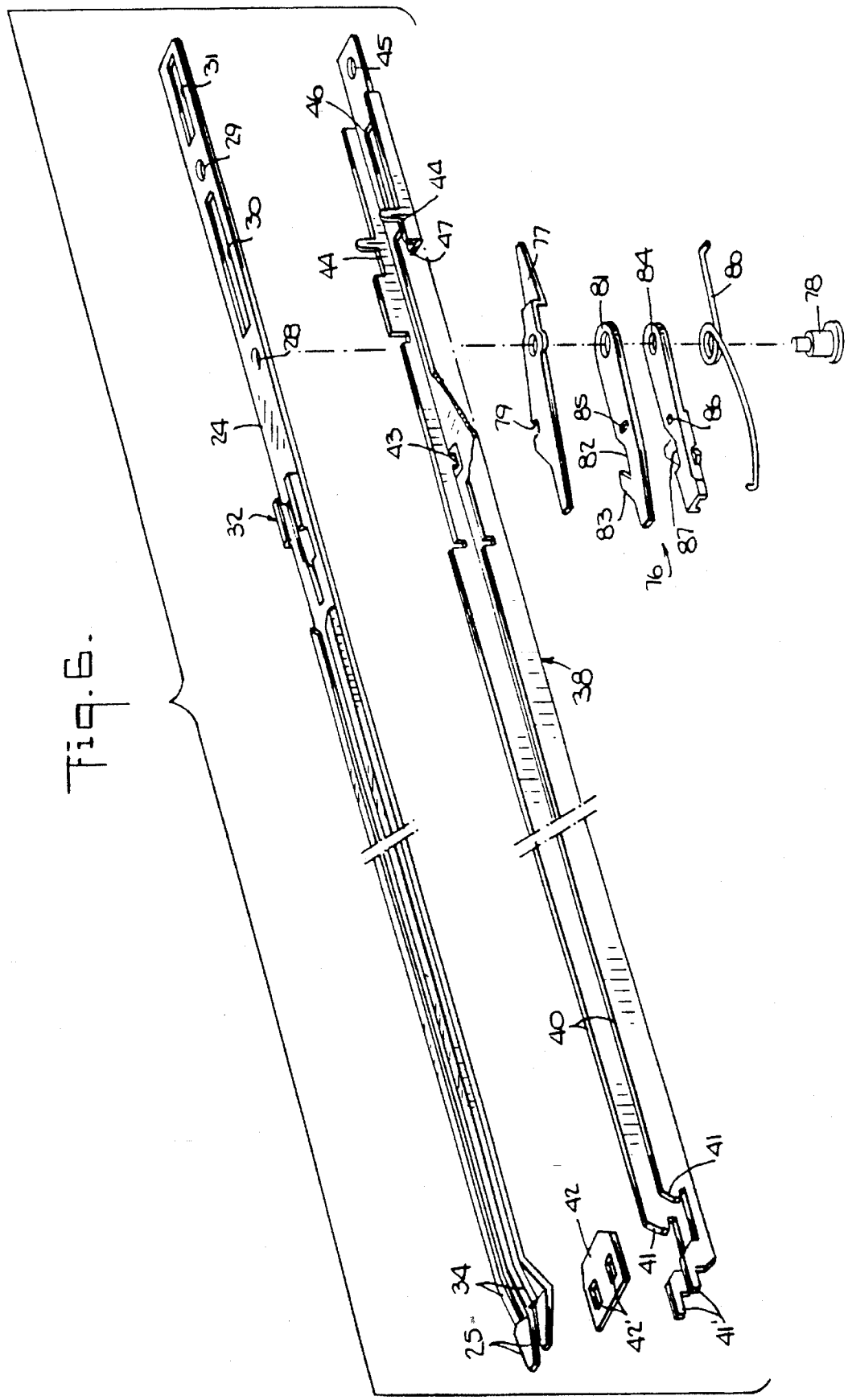
FIG. 6 illustrates an exploded view of the jaw blade assembly, clip carrier, channel assembly and latches for the pusher bar and channel assembly.

Referring to FIG. 1, the surgical clip applicator 11 includes a housing 12, a jaw blade assembly 13 fixedly connected to the housing 12, a channel assembly 14 slidably mounted in the housing 12 and enveloping the jaw blade assembly 13, a pusher bar 15 slidably mounted in the channel assembly 14 and means 16 for moving the pusher bar 15 and the channel assembly 14 relative to each other. The means 16 for moving the channel assembly 14 and pusher bar 15 includes a pair of handles 17 pivotally connected to opposite sides of the housing 11 by link means in the form of a pair of links 18 connected to and between the handles 17 and the channel assembly 14 for moving the channel assembly in a distal, i.e. forward, direction in response to closing of the handles 17 together and a second link means in the form of two pairs of links 19, 20 connected to and between the handles 17 and the pusher bar 15 for moving the pusher bar 15 to a proximal-most position in response to closing of the handles 17 together.

Referring to FIGS. 1 and 2, the housing 12 is formed of a bottom 21 and a top 22 which are secured together as by three rivets 23. This housing 12 is of slender construction and is made of any suitable material, for example, a plastic material. As indicated, the housing bottom 21 is contoured and recessed so as to receive various components of the applicator as further explained below. The housing top 22 is contoured for similar purposes.

The handles 17 are pivotally connected at the distal ends to opposite sides of the housing 11 by means of the pair of rivets 23 at the forward end of the housing.

Referring to FIG. 7, the jaw blade assembly 13 includes an elongated jaw blade 24 which has a pair of upwardly angled jaws 25 formed at a bifurcated distal end for receiving a surgical clip therein. As is conventional, each jaw 25 is provided with a small slot or groove in a side wall so as to receive a leg of a substantially U-shaped surgical clip therein. In addition, a tissue stop 26 is disposed below the jaws 25 and extends proximally under the jaw blade 24. This tissue stop 26 has a bifurcated distal end which underlies and serves as a guide to prevent tissue from impeding movement of the clip 33 (FIG. 4) into jaws 25. The jaw blade 24 is shaped so that the jaws 25 can be cammed towards each other and spring-biased apart.

The jaw blade 24 is also provided with an upstanding abutment 27 at an intermediate point to act as a distal stop for the pusher bar 15. In addition, the rear end of the jaw blade 24 is provided with an alternating sequence of circular openings 28, 29 and elongated slots 30, 31 for purposes as explained below.

The jaw blade assembly 13 also includes a clip carrier 32 for supplying a series of clips 33 to the jaws 25. This clip carrier 32 is formed as an elongated channel having a pair of side walls or rails 34 between which the clips 33 are slidably guided, a pusher 35 (see FIG. 4) which slides between the rails 34 and a spring 36 for biasing the pusher 35 in a distal direction. As indicated in FIGS. 3 and 4, the spring 36 is mounted about a shaft 36' which has a head to abut at the proximal end against an abutment 37 of the clip carrier 32 (FIG. 7) and fits over a stem 35' on the pusher 35 (FIG. 4) in order to bias the pusher 35 in the forward position.

Referring to FIG. 9, the rails 34 are aligned with the jaws 25 and are angled downwardly so as to deliver a clip directly from between the rails 34 to directly between the jaws 25 and are spaced apart a distance equal to the spacing between the jaws 25.

Referring to FIG. 4, the channel assembly 14 includes an elongated channel shaped member 38 and a cover 39 which is fixedly secured to the channel shaped member 38 in order to envelope the jaw blade assembly 13 of FIG. 7.

As indicated in FIG. 6, the channel 38 has a pair of upstanding parallel walls 40 which extend to a distal end. Each wall 40 is shaped at the distal end to form a recess 41 and an axially extending projection 41'. A capture plate 42 serves to hold down the jaw blade 24 and is disposed between the jaw blade 24 and the clip carrier 32. Also, as indicated in FIG. 1, the channel cover 39 is inclined downwardly at the distal end in alignment with the distal ends of the walls 40.

In addition, the channel 38 has a depending detent 43 (see FIG. 6) at an intermediate point of the bottom of the channel 38 as well as a pair of recesses 44 formed in the walls 40 towards the proximal end. In addition, the proximal end of the channel 38 is formed with a circular opening 45 and two elongated slots 46, 47.

Referring to FIG. 4, the pusher bar 15 is of elongated shape and has a depending nose 48 at the distal end. Nose 48 includes a pair of members 48a which extend substantially transverse to the longitudinal axis. Each member 48a includes a distally facing clip contacting surface 48b and an angular cam surface 48c proximal to the clip contacting surface. As indicated, the forward end of the pusher bar 15 is angled slightly downwardly from the remainder of the bar 15 and is located above the clip carrier 32 so as to slide on the bottom of the carrier 32. In addition, the pusher bar 15 has a depending detent 49 which is secured thereto in any suitable fashion. This detent 49 is shaped as indicated in FIG. 10 to extend rearwardly, i.e. in the proximal direction for purposes as explained below and has a secondary detent 49' at the distal end. As illustrated, the proximal end of the pusher bar 15 is provided with an elongated slot 50.

Referring to FIGS. 1 and 4, a sleeve 51 in the form of a shrink-fitted plastic tube is disposed about the channel assembly 14 for conventional purposes.

Referring to FIG. 1, each handle 17 is articulated to the housing 12, the channel assembly 14 and the pusher bar 15 in similar relation. Hence, only one articulation will be discussed. As indicated in FIG. 8, each channel link 18 is pivotally mounted at the proximal end about a pivot pin 52 which is fixed within the handle 17 while being pivotal about a pivot pin 53 (see FIG. 1) at the distal end which is secured in the circular opening 45 of the channel 38 of the channel assembly 14 (see FIG. 6). Thus, when the handles 17 close together, the two channel links 18 push the channel assembly 14 (see FIG. 1) forwardly in the distal direction. At this time, the channel assembly 14 slides over the jaws 25 to close the jaws 25 together so as to crimp a clip 33 positioned therebetween.

Each pusher bar link 19 is pivotally mounted about a fixed pin 54 mounted in the housing 11 (see FIG. 2). In addition, the proximal end of each link 19 is pivotally mounted about a pivot pin 55 which is slidably mounted within an elongated groove or channel 56 in the handle 17. The pivot pin 55 also receives the distal end of the pusher bar link 20. The proximal end of this link 20 is mounted about a common pin 57 (see FIGS. 1 and 2) which, in turn, slides within the elongated slot 50 of the pusher bar 15.

As indicated in FIG. 8, each handle 17 is provided with two slots 58 to accommodate the links 18, 19, 20. In addition, a cover plate 59 is mounted over an opening in each handle via depending pins 60 to close off the groove 56 and cover over the assembly opening.

When the handles 17 are brought together, the links 18 slide the channel assembly 14 forward (distally) while the links 19, 20 initially expand apart so that the pin 57 of link 20 (see FIG. 1) slides within the slot 50 of the pusher bar 15 until abutting against the proximal end of the pusher bar 15. Thereafter, the pusher bar 15 is moved in the proximal, i.e. rearward direction relative to the housing 11. Thus, when the handles 17 are first brought together, the channel assembly 14 moves inwardly and after a slight delay, the pusher bar 15 begins to move proximally. For example, the channel assembly 14 moves approximately 0.060 inches before the pusher bar 15 begins to move.

Referring to FIGS. 1 and 5, a spring assembly 60 is provided in the housing 12 in order to bias the channel assembly 14 in a proximal direction against the force of the handles 17. As indicated in FIG. 5, the spring assembly 60 is formed of a backing block 61, for example of plastic which has a pair of upstanding ears 62 through each of which a bore 63 passes. In addition, a pair of shafts 64 extend through the bores 63 of the block 61 and receive compression springs 65 thereon. Each shaft 64 has an enlarged head at the distal end for abutting against a suitable abutment surface of the housing top 22 (not shown) as well as a flanged stop 66 at the proximal end for sub-assembly purposes. As indicated in FIG. 3, the backing block 61 is mounted in the channel assembly 14 and specifically within and across the recesses 44 formed in the walls 40 of the channel 38.

Referring to FIG. 2, a spring assembly 67 is also provided for biasing the pusher bar 15 in the distal direction. To this end, the spring assembly 67 has a shaft 68 which has an enlarged and shouldered head 69 at the distal end which fits into an opening of a depending lug 70 on the pusher bar 15 as well as a spring 71 which fits over a reduced portion of the shaft 68 and which abuts against a suitable abutment (not shown) in the housing bottom 21. As indicated in FIG. 3, the lug 70 projects through a slot in the channel assembly 38 formed by a reduced section of a wall 40 and the cover 39.

Referring to FIGS. 11 and 12, a retaining means 72 is provided on the carrier 32 in order to retain the nose 48 of the pusher bar 15 when the carrier 32 has been emptied. The retaining means 72 is in the form of a channel-shaped member which is secured to the underside of the carrier 32 and which has a pair of upstanding walls 73, each of which provides a cam surface 84 for sliding of a clip 33 thereon. The member also has an opening 75 formed in the floor which is sized to receive the nose 48 of the pusher bar 15 in the absence of a clip 33.

Referring to FIG. 4, a locking means 76 is provided for blocking the jaws 25 against movement towards each other in response to the nose 48 of the pusher bar 15 being retained in the locked position, i.e. in the opening 75 (see FIG. 12). This position is obtained when there are no longer any clips 33 in the clip barrier 32. In this respect, the distal end of the pusher bar 15 is spring biased into the clip carrier 32 so that when clips 33 are present, the distal most clip 33 is pushed by the pusher bar nose 48 onto and across the cam surface 74 of the upstanding walls 73 of the retaining means 72 which cams the retaining means away from the distal end of the pusher bar 15 thus allowing the nose 48 to pass over the opening 75 when a clip is being pushed forwardly into and between the jaws 25. However, with no clips remaining, the retaining means 72 is not cammed away from the distal end of the pusher bar 15, thus not allowing the nose 48 to pass over the opening 75 but to drop into the opening 75 stopping the forward motion of the pusher bar 15.

Figure 13A:
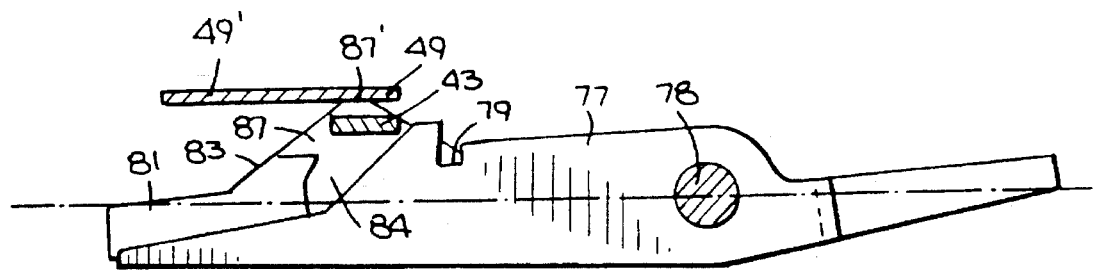
FIG. 13A illustrates a normal position of the locking mechanism.
Figure 13B:
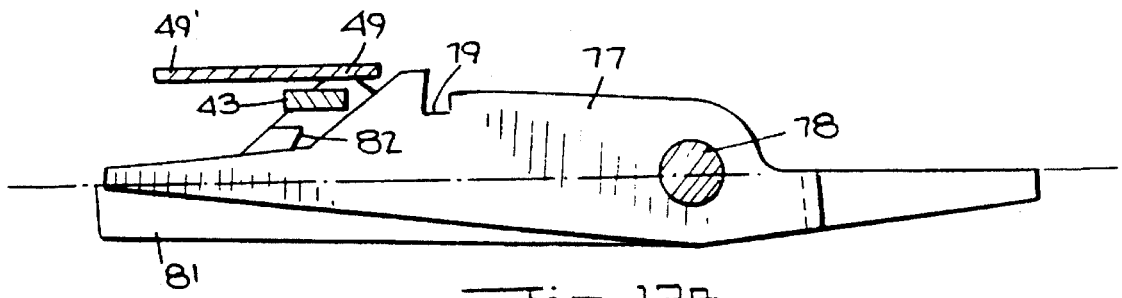
FIG. 13B illustrates a position of the locking mechanism upon initial squeezing of the handles.
Figure 13C:
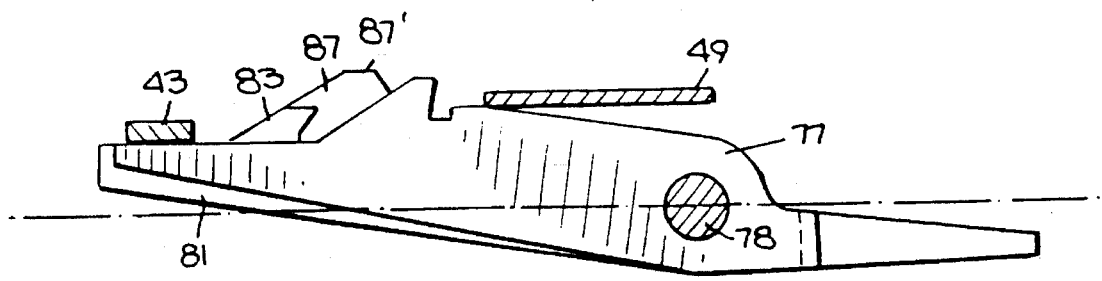
FIG. 13C illustrates a position of the locking mechanism with the handles fully closed.
Figure 13D:
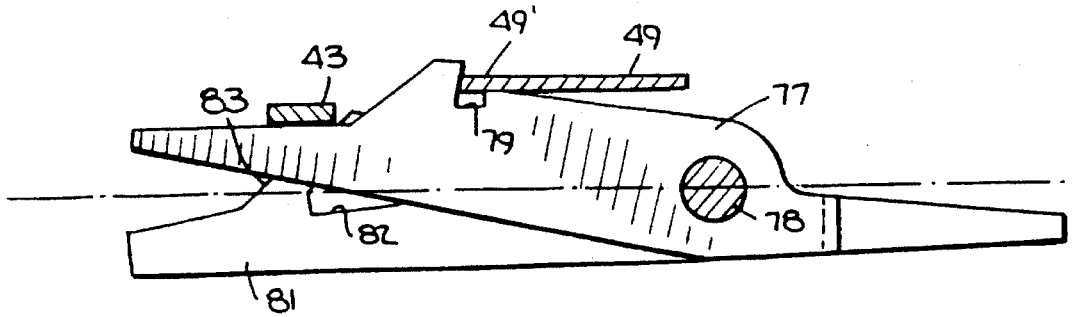
FIG. 13D illustrates a position of the locking mechanism during a return stroke.
Figure 13E:
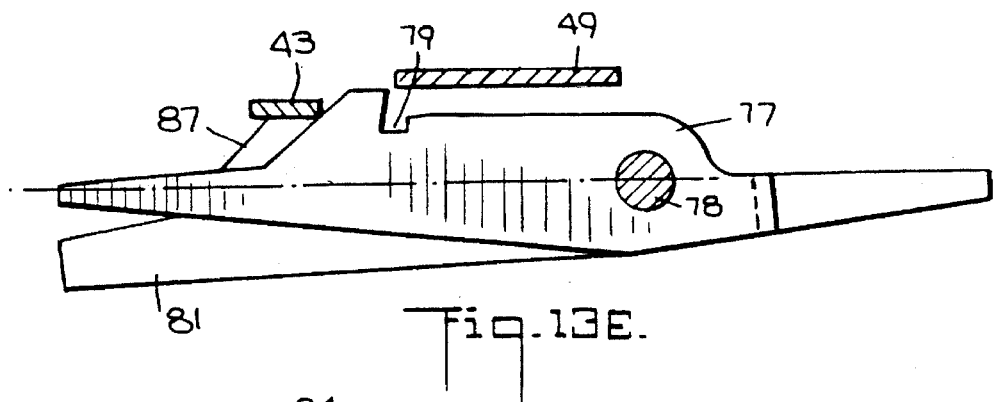
FIG. 13E illustrates a position of the locking mechanism at the release point of the pusher bar.

As shown in FIG. 6, the locking means 76 includes a latch 77 which is pivotally mounted about a rivet 78 which is fixed to the circular opening 28 of the jaw blade 24. As indicated, the rivet 78 extends upwardly into the circular opening 28 of the jaw blade 24 as well as through the elongated slot 47 in the channel 38 of the channel assembly 14. The latch 77 is pivotally mounted below the channel 38 and has a recess 79 for selectively engaging with the depending detent 49 of the pusher bar 15 (see FIG. 10). In addition and as shown in FIG. 13D, the latch 77 is spring biased by a spring 80 so as to pivot in a clockwise manner as viewed so as to engage with the detent 49' of the pusher bar 15 when the pusher bar 15 is in its proximal position preventing premature feeding of the distal most clip into the jaws 25.

The locking means 76 also includes a second latch 81, for example of sheet metal, which is pivotally mounted on the rivet 78 in parallel relation to the latch 77. This latch 81 has a recess 82 and a cam surface 83 forward of the recess 82 to cooperate with the depending detent 43 of the channel 38 of the channel assembly 14.

The locking means 76 also includes an elongated cam follower 84, for example of plastic which is also pivotally mounted above the rivet 78 in single-arm fashion. This cam follower 84 is fixed to the latch 81 via a detent 85 of the latch 81 fitting into a rectangular hole 86 in the follower 84 so as to pivot therewith and includes a cam surface 87 of triangular shape which faces toward the detent 49 of the pusher bar 15 when the applicator is in a normally opened position. In addition, the cam follower 84 is biased by one end of the spring 80 in a clockwise direction (as viewed) to bias the latch 81 towards engagement with the detent 43.

Figure 13F:
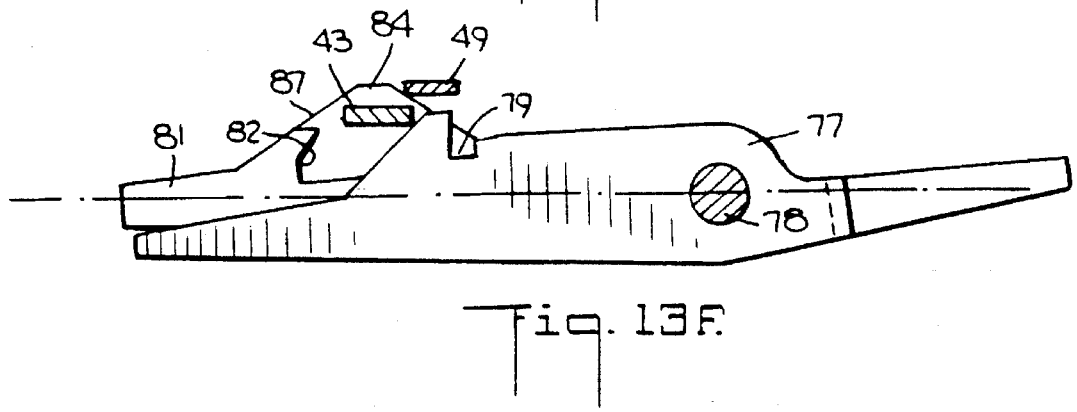
FIG. 13F illustrates a position of the locking mechanism with a clip at a distalmost position in the clip carrier.

Should the clip barrier 32 contain clips 33, the nose 48 of the pusher bar 15 will normally be placed in a distal-most position immediately behind the jaws 25. At this time, the detent 49 on the pusher bar 15 will be located against the high point 87' of the cam surface 87 of the cam follower 84 (see FIG. 13A). Thus, the latch 81 for locking the channel assembly 14 in place will b out of line with the detent 43. As the handles 17 (see FIGS. 13B and 13C) are squeezed together, the pusher bar detent 49' will slide proximally past the recess 79 of the latch 77 while the detent 43 of the channel assembly 14 slides distally past the recess 82 of the latch 81. As the handles open with clips in the clip carrier 32, the detent 43 of the channel assembly 14 slides on the cam surface 83 into alignment with the recess 82 of the latch 81 (FIGS. 13D, E and F). At the same time, the detent 43 of the channel assembly 14 rotates the latch 77 counter clockwise releasing detent 49' distally. As the pusher bar 15 moves distally, the detent 49 comes in contact with the cam surface 87 of the cam follower 84 rotating the cam follower 84 counter clockwise as the pusher bar 15 moves distally moving surface 82' of recess 82 of the latch 81 out of line with detent 43 of the channel assembly 14. When the pusher bar is at its distal most position (FIG. 13F), the distal side of a cross bar 15' of the pusher bar 15 (see FIG. 4) abuts the proximal side of the jaw abutment 27.

Figure 14:
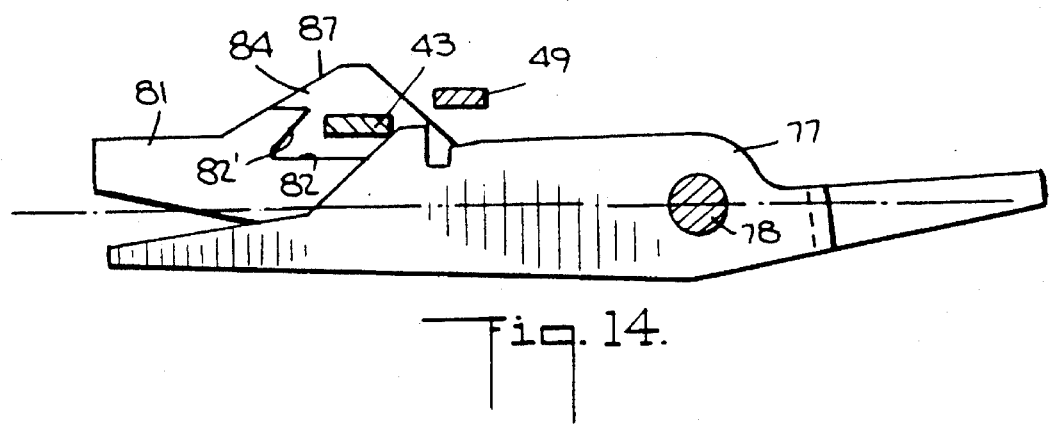
FIG. 14 illustrates a position of the locking mechanism with no clip in the carrier.
Figure 15:
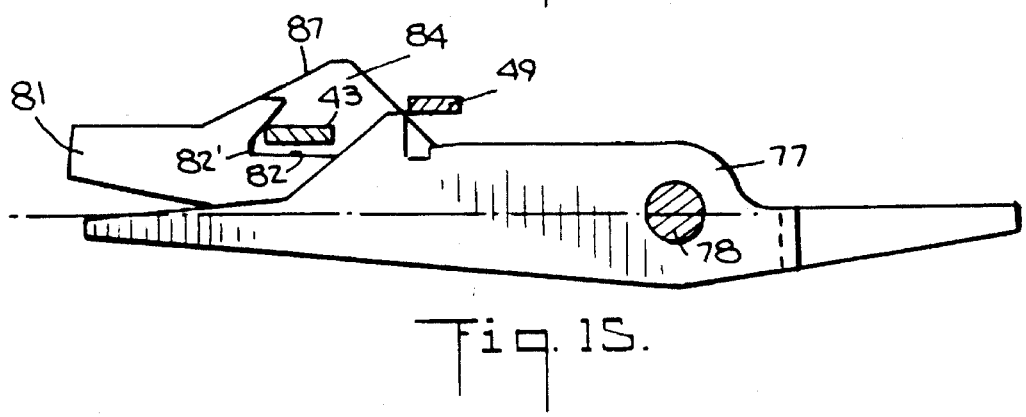
FIG. 15 illustrates a position of the locking mechanism upon partial squeezing of the handles in the locked position.

However, should the clip carrier 32 be empty, the nose 48 of the pusher bar 15 will drop into the opening 75 causing the detent 49 to stop at a position away from cam surface 87 of the follower 84 leaving surface 82' of recess 82 of latch 81 in line with detent 43 of channel 38 (FIG. 14) upon a subsequent initial squeezing together of the handles of the applicator (FIG. 15), the spring biased latch 81 and associated cam follower 84 will be in a position such that surface 82' of recess 82 of the latch 81 will impede the movement of the detent 43 of the channel assembly 14. In this respect, the detent 49 of the pusher bar 15 is not in a position against the cam surface 87 so as to preclude a clockwise pivoting motion. Thus, as the handles are squeezed further, the detent 43 comes into contact with surface 82' of the recess 82 of the latch 81 causing latch 81 to rotate clockwise and is prevented from further distal motion. The jaws 25 can, thus, not be brought together and the handles are prevented from a further closing movement.

When the applicator 11 is to be used, the handles are first squeezed together causing the channel assembly 14 to move forwardly and the pusher bar 15 to move rearwardly into a position to feed the first clip 33 from the carrier 32. As the pusher bar 15 starts to move rearwardly, the pusher bar latch 77 is biased to rotate into the path of the detent 49 on the pusher bar 15 and after passage of the detent rearwardly thereby prevents the pusher bar 15 from moving forward prematurely. As the handles are released, the channel assembly 14 moves in the rearward direction on a return stroke while the pusher bar 15 remains stationary until the channel assembly 14 has moved close to its rearward position at which time the depending detent 43 of the channel 38 rotates the pusher bar latch 77 in an opposite direction, i.e. counter clockwise as viewed in FIG. 6, releasing the pusher bar 15 to feed the first clip 33 between the jaws 25. At this time, the pusher bar 15 springs forwardly under the bias of the spring assembly 67 (see FIG. 2) with the nose 48 passing over the opening 75 in the retaining means 72 since the clip 33 in the carrier 32 moves the retaining means 72 away from the bar 15 allowing the nose 48 to pass over the opening 75 of the retaining means. With the applicator 11 thus prepared, a surgeon will be able to see a clip in place and can then apply the clip where desired by squeezing the handles 17 together. At this time, when the handles are released, the next clip in the carrier is pushed into place between the jaws.

A surgical clip applicator is thus provided which is able to provide a clip between the jaws of the applicator in a ready position for firing upon squeezing of the handles together. This initial positioning of the clip in place permits a surgeon not only to visually check to see if a clip is present in the jaws but also permits the surgeon to position the clip about a vessel or other tissue which is to be clipped.

A surgical clip applicator is also provided which has a self-locking arrangement which prevents closing of the handles together when there are no clips remaining in the applicator.

Still further, a surgical clip applicator is provided which is of relatively simple compact and slender construction which can be readily manipulated by a surgeon during a surgical procedure.

Figure 16:
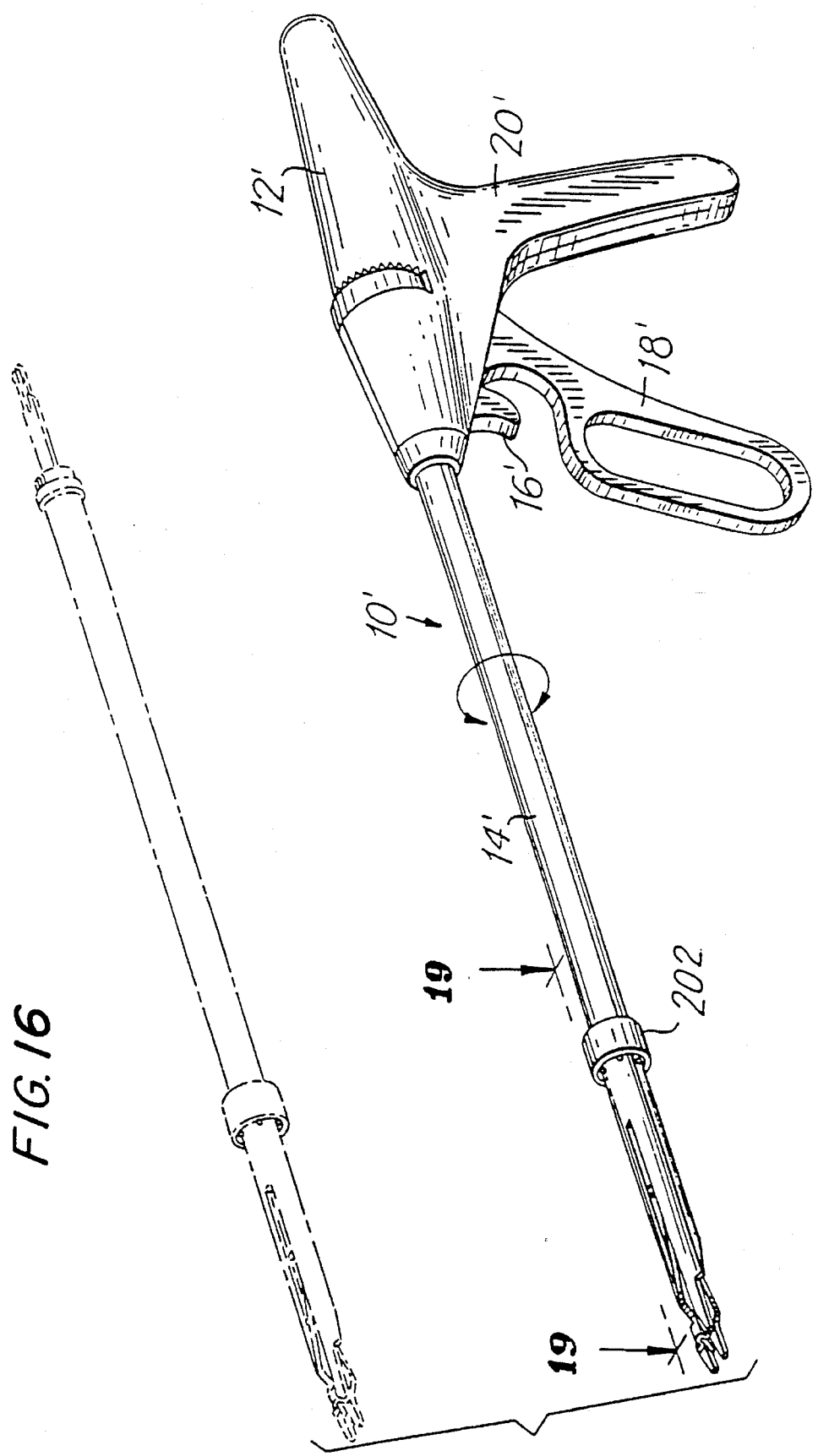
FIG. 16 is a perspective view of a disposable apparatus for placing clips in laparoscopic or endoscopic procedures.

A further surgical clip applying apparatus will now be discussed. Referring initially to FIG. 16, an apparatus for applying clips in endoscopic and laparoscopic procedures is disclosed in perspective view. The apparatus is preferably constructed as a disposable item of several materials as will be described. Essentially, however, two basic materials are used, i.e., a polycarbonate material such as LEXAN brand plastic material by General Electric Company and stainless steel. Other suitable materials are contemplated.

Briefly, apparatus 10' includes two main sections. A handle section 12' and an endoscopic section 14' which is distal of the handle section. A clip pushing system which will be described hereinbelow is operative by single finger operative trigger 16' and a clip clamping mechanism is operative by squeezing handle 18' toward hand grip 20' using multiple fingers of the operator. A safety locking device 202 which will be described in detail hereinbelow pertains to the use of the apparatus with a cannula such as a trocar guide tube, which is inserted into an aperture formed by a trocar in the patient's body. As will be seen from the description which follows, device 202 prevents use of the instrument with a cannula of incorrect size.

Referring now to FIGS. 17 and 19–29 in conjunction with FIG. 16, the endoscopic section 14' of the apparatus 10' will now be described. The endoscopic section 14' is preferably housed in a non-removable cartridge formed of upper half section 15a and lower half section 17'. Each half section is formed of a material capable of withstanding the stresses applied by the inner working compartments without deformation or compromise of precision. A polycarbonate material such as LEXAN brand material marketed by General Electric Corporation has been found to satisfy the requisite strength and deformation requirements. Other suitable materials may be used. If desired, the cartridge can be constructed to be removable from the handle.

The lower housing half section 17' includes upstanding tabs 16a and the upper housing half section 15a includes correspondingly positioned slots (not shown) which are dimensioned to receive the upstanding tab 16a such that the two half sections may be attached by ultrasonic welding techniques. Preferably, the slots are dimensioned to receive the upstanding tabs 16a in interference relation to assist securement of the half portions together. Alternatively, the half sections may be adhesively attached. Further, upper half section 15a includes longitudinally extending slots 15a' which receive correspondingly dimensioned ribs in the collar of the handle section (to be described) to facilitate rotation of the endoscopic section with the collar.

Referring once again to FIG. 17, a plurality of U-shaped clips 22' are positioned within the housing for movement in the distal direction in preparation for the clamping procedures. The clips are preferably of titanium for use in clipping blood vessels such as arteries. This material avoids the "starburst" effect and facilitates enhanced CT imaging. The clips 22' are aligned in a row as shown, with the leg portions facing distally. A jaw blade 26' is positioned at the distal end and includes a pair of jaws 24' for reception of each clip whereby the jaws are brought together to close the clip about the artery.

The jaw blade 26' is fabricated of a material having sufficient resilience such that clamping of the distal pair of jaws 24' toward each other to close a clip therebetween will be followed by return of the jaws to their original position upon release of the clamping forces. Stainless steel has been found to be a preferred material capable not only of withstanding the requisite number of clamping cycles without adverse affect, but also of being suitably sterilized. Furthermore, jaw blade 26' includes three square shaped apertures 28' dimensioned to receive three correspondingly shaped pins 30' molded into the lower body half section 17' of the housing to position the jaw blade 26' with respect to the body.

Figure 17:
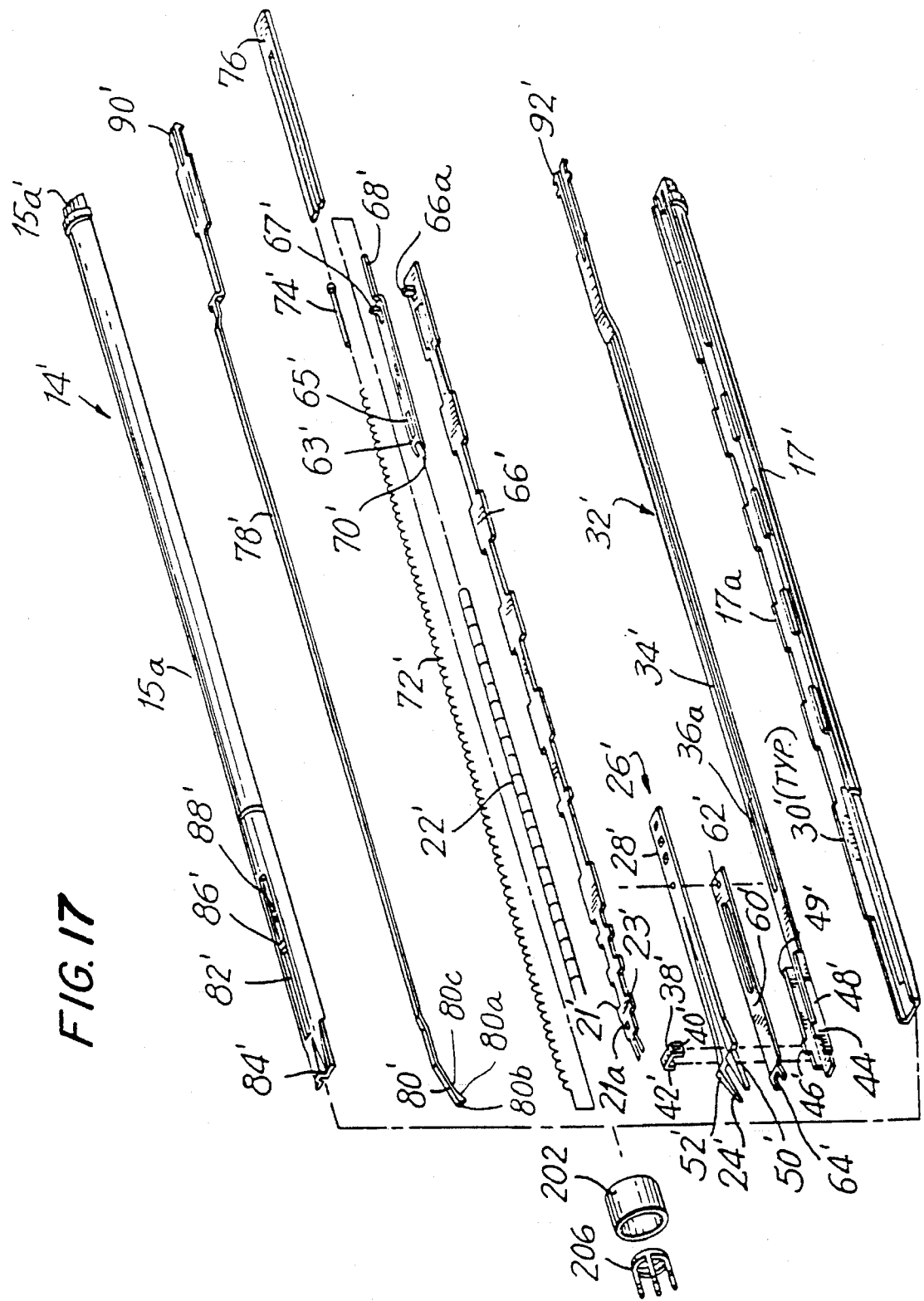
FIG. 17 is a perspective view with parts separated for purposes of illustration of the endoscopic section of the apparatus of FIG. 16.

Referring further to FIG. 17, crimping channel 32' is dimensioned and positioned for slidable movement within the body of the housing and defines elongated slot 34' having a wider portion 36a at the distal end for reception of square pins 30'. The width of the slot 34' in distal portion 36a of crimping channel 32' is just sufficient to receive the pins 30' to maintain relative alignment between the jaw blade 26' and the pins 30'. A channel bracket 38', also preferably of stainless steel, is positioned atop the jaw blade and defines two downwardly extending side walls 40', 42' positioned to be welded to the distal portions of correspondingly positioned and dimensioned upwardly extending side walls 48', 49' of crimping channel 32'. This channel bracket 38' is positioned just distally of upstanding tabs 44', 46'. It will be appreciated that the crimping channel 32' forms with channel bracket 38', a rectangular slidable housing surrounding the jaws 24' of jaw blade 26'. Moreover, since the jaw members 24' are formed of outwardly tapered side walls 50', 52', movement of the crimping channel 32' in the distal direction will cause inward movement of the jaw members, while movement of the crimping channel in the proximal direction will result in corresponding proximal movement of channel bracket 38' thereby relieving the jaw members 24' of the crimping forces and permitting the jaw members to open.

Figure 30:
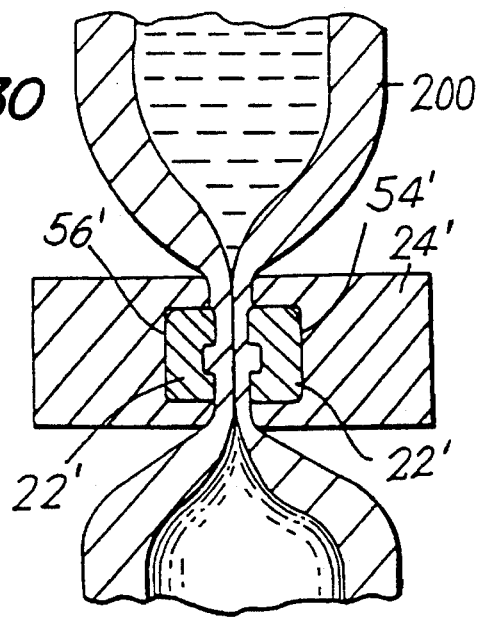
FIG. 30 is a cross-sectional view taken along lines 30—30 of FIG. 27.
Figure 29:
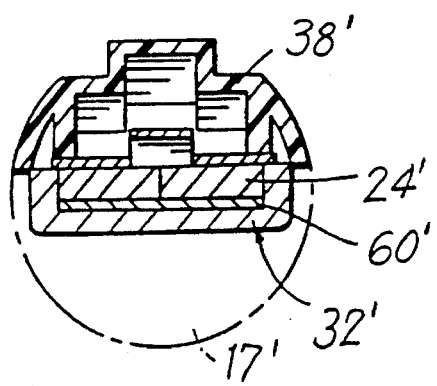
FIG. 29 is a cross-sectional view taken along lines 29—29 of FIG. 27.

Referring now to FIGS. 17 and 30, jaw members 24' include generally longitudinal grooves 54', 56' dimensioned to receive a clip 22' therebetween for clipping a body portion. Tissue stop plate 60' shown in FIG. 17, is positioned between jaw blade 26' and crimping channel 32' and includes aperture 62' at the proximal end portion for reception of an appropriate pin (not shown) which extends through the jaw blade 26' and tissue stop plate 60' to maintain alignment of the jaw blade 26' and the tissue stop plate 60' when these components are welded together. At the distal portion of the tissue stop plate a tab 64' is oriented at approximately the same downward angle as the jaws 24' for alignment therewith and includes an arcuate cut-out portion as shown, dimensioned to snugly receive an artery for locating and positioning the artery in the precise area within the jaw blades as required for applying a clip to the artery with predetermined precision. The tissue stop plate is preferably fabricated of a thin stainless steel sheet material.

Referring further to FIG. 17, cover plate 66' is appropriately dimensioned to rest atop the clip clamping mechanism described hereinabove, and supports the row of clips 22'. Proximally of clips 22' is positioned a clip follower 68' which is "U" shaped at the distal end to snugly engage and advance the clips under the action of clip feed spring 72' connected thereto at the distal end and to a pin 74' at the proximal end. Pin 74' is in turn connected to cover plate pin anchor tab 66a while clip pusher bar 78' is positioned for slidable movement thereon between a proximal position and a distal-most portion. When the next clip 22' is engaged by the distal nose 80' of clip pusher 78', distal movement of the clip pusher 78' advances the clip into the slots 54', 56' of jaws 24' of the jaw blade 26'. Nose 80' includes a pair of members 80a which extend substantially transverse to the longitudinal axis. Each member 80a includes a distally facing clip contacting surface 80b and an angular cam surface 80c proximal to the clip contacting surface.

Referring again to FIG. 17, upper housing half section 15a includes a longitudinal slot 82' having bridge connections 84', 86', 88' as shown. In position, the clip pusher bar 78' is snaked over bridge 88' and under distal bridges 86' and 84' such that bridge 88' will act as a stop mechanism to prevent the advancement of clip follower 68' when upstanding tab 67' engages bridge 88' as shown in FIG. 20a. This occurs when the last clip 22' has been advanced and crimped, thereby permitting the clip follower to advance to its distal-most position under action of spring 72'.

Thus by sliding clip pusher bar 78' between the proximal and distal positions, the clip pusher bar may be alternately positioned with nose 80' behind each successive clip, and thereafter advancing the clip into the jaws 24' of jaw blade 26' by a pusher mechanism in handle section 12' which will be described. The connection between the mechanism in the handle 12' is made with the proximal end portion 90' of clip pusher 78' which extends into the handle section. Further, the connection between the appropriate link of handle 12' with the crimping mechanism of jaw blades 24' is made with the proximal end portion 92' of crimping channel 32' as will be described. The precise action of the handle 12' and its inner mechanism is such that proximal force applied to trigger 16' causes clip pusher 78' to push the next clip 22' into the jaws 24' while simultaneously releasing the crimping channel 32' to the "ready" position for crimping the clip. Next, the operator squeezes handle 18' toward hand grip 20' which causes crimping channel 32' to move distally to crimp the clip positioned within jaws 24', while simultaneously moving clip pusher 78' proximally in position to push the next clip 22' into the jaws 24'. These movements are alternately repeated until the last clip 22' is spent.

Figure 18:
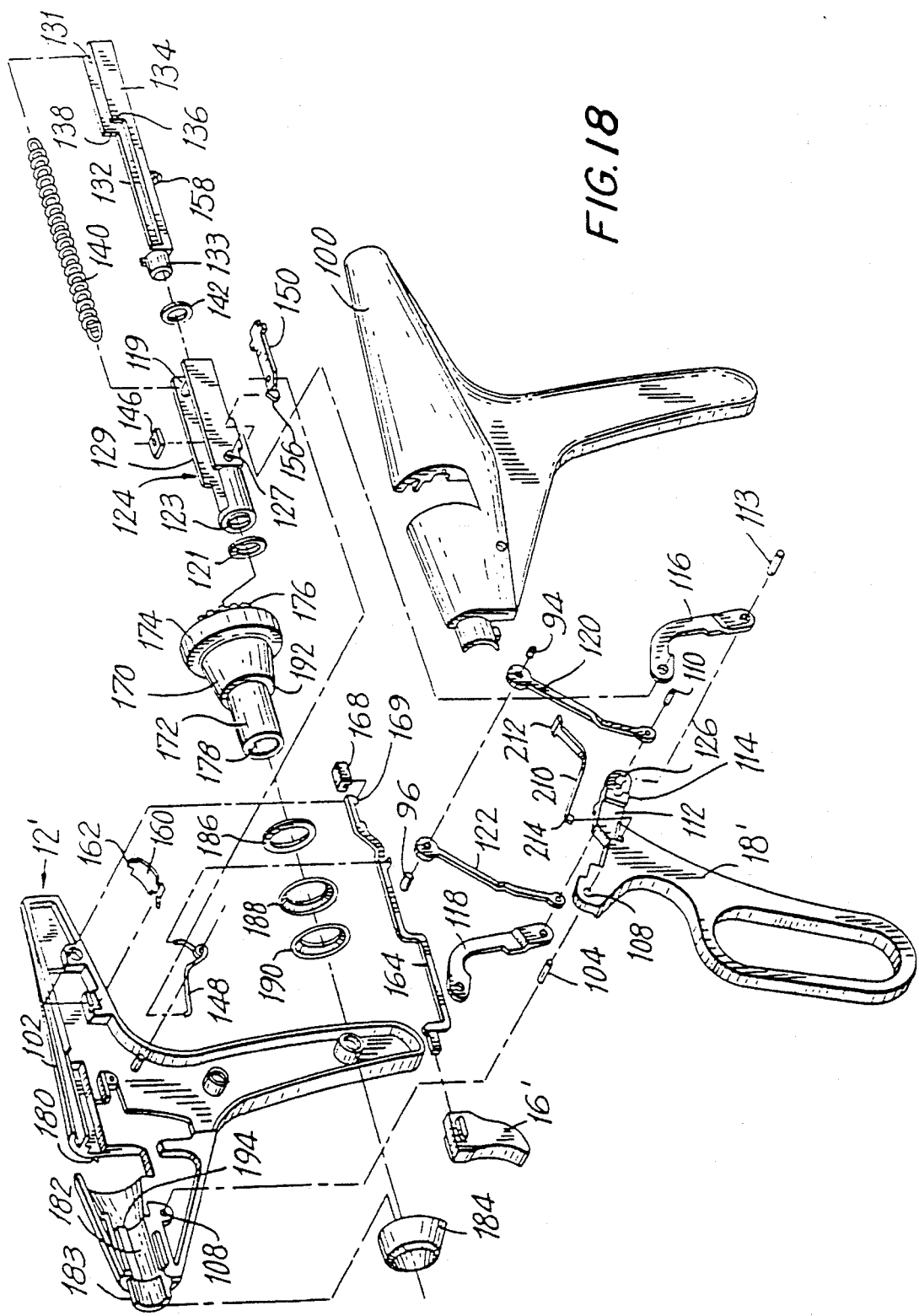
FIG. 18 is a perspective view with parts separated for purposes of illustration of the handle section of the apparatus of FIG. 16 utilized for activating the endoscopic section.

Referring to FIG. 18 the handle section 12' of the apparatus is illustrated with the transmission mechanism for manually activating the endoscopic section described previously, i.e., advancing clips distally and crimping the clips about an artery. The parts of the handle section 12' are separated for convenience of illustration. The handle section 12' includes left body 100 and right body 102. The body parts are fastened together by fasteners such as screws or rivets extending through appropriate bosses. Alternatively, the body parts may be ultrasonically welded or adhesively attached together along their seams or by bosses and transverse rods or pins in engaged relation. The body parts 100, 102 are preferably fabricated of a hard plastic material such as LEXAN Brand polycarbonate material marketed by General Electric Co. Other rigid materials are contemplated. Materials capable of being molded into shape while being able to sustain the forces applied by the transmission mechanism are preferred.

The clip loading and crimping system is divided into two separate systems as described in connection with the endoscopic section. As noted, a first system pushes the clip next in line from a row of clips to a position within a pair of clamping jaws 24' as described in connection with the endoscopic section of the apparatus. The second system closes the pair of jaws 24' around the clip to cause the clip to grip the intended artery, tissue, or other blood vessel, while simultaneously repositioning the clip pusher mechanism to push the clip next in line into position between the jaws. This procedure is repeated alternately and sequentially until all clips are spent.

Referring now to FIGS. 31–34, in conjunction with FIG. 18, the clip pusher and clamping loading mechanism will now be described. Handle 18' is pivotally mounted via aperture 108 on pin 104 extending transversely of the body parts. The handle 18' includes a rearward extension 112 which defines arcuate slot 126 through which pin 110 extends. Pin 113 extends through aperture 114 and functions as a pivot for left channel link 116 and right channel link 118 which extend in a generally forward direction. Rearwardly directed left pusher link 120 and right pusher link 122 are mounted for pivotal motion on pin 110 extending through arcuate slot 126.

At the opposite ends left channel link 116 and right channel link 118 are pivotally mounted to channel tube 124 by pivot pins 127, 129 formed integral therewith and pusher links 120, 122 are connected to transverse pins 94', 96' arranged for slidable movement within the forward cut-out portion 132 of pusher tube 134 for engagement with shoulders 136, 138 of the pusher tube when the links are moved in the proximal direction. Main spring 140 connects channel tube 124 with pusher tube 134 via pins 119, 131, such that the spring is loaded when the tubes are separated by squeezing handle 18 toward handle grip 20 causing distal movement of channel tube 124 and proximal movement of pusher tube 134.

Referring now once again to FIGS. 18 and 31 in conjunction with FIG. 17, it can be seen that pusher tube 134 is connected to clip pusher bar 78' by proximal end tabs 90' which are inserted by squeeze and release action into the distal opening 133 of pusher tube 134 with annular steel pad 142 positioned as an interface between the plastic pusher tube and the steel pusher bar. Similarly, the crimping channel 32' is connected to the channel tube 124 by insertion of the proximal legs 92' into the distal opening 123 of channel tube 124 with annular steel pad 121 positioned as an interface between the plastic channel tube 124 and the steel legs 92'. With the connections described, the crimping channel and clip pusher are free to rotate independently of the channel tube and pusher tube as permitted by the rotation of the proximal legs 90' and 92', within the distal opening 133 of pusher tube 134 and opening 123 of channel tube 124.

Referring once again to FIG. 18, latch plate 150 is pivotally mounted and biased upward toward apertured plate 124 in lower wall of channel tube 124 by spring 148 such that tongue 156 enters the aperture of plate 146 when the channel tube 124 is moved to its proximal position. This prevents unwanted forward movement of the channel tube 124 prior to advancing a clip in position within jaw members 24' of jaw plate 26'. Release of tongue 156 is accomplished by engagement of the latch plate 150 by pin 158 extending downwardly from pusher tube 134 when pusher tube moves distally under action of mainspring 140 as will be developed further. Similarly, pusher release leaf spring 160 is positioned for entry of tab 162 into a slot 161 in the bottom wall of pusher tube 134 when the tube is moved proximally by pusher links 120, 122 against the force of mainspring 140, permitting the leaf spring 160 to retain the pusher tube in position against the force of the mainspring 140. Release of the pusher release leaf spring 160 is accomplished by proximal movement of release lever 164 via finger activated pusher release button 16 supported at the proximal end by lever support block 168 which slidably moves against the lower wall of pusher tube 134.

In operation, squeezing the handle 18' toward hand grip 20' causes pusher links 120, 122 to pivot and move proximally, resulting in proximal movement of pusher tube 134 by engagement of pins 94', 96' with shoulders 136, 138 of pusher tube 134. Proximal movement of pusher tube 134 continues with pusher release spring 160 continuously biased upwardly until tab 162 enters the slot 161 in the bottom wall of pusher tube 134 thereby retaining pusher tube 134 in position against the bias of mainspring 140. Simultaneously, this action withdraws clip pusher 78' to a position just proximal of the next clip 22' in preparation for pushing the clip distally between the jaw members 24' of jaw blade 26'. Retention of the pusher tube in this proximal position by release spring 160 also retains the clip pusher 78' in the corresponding position until the clip next in line is to be pushed into the jaws 24'. When this is desired, proximal movement of pusher release button 16' causes proximal movement of release lever 164 and engagement of proximal tip 169 with pusher release spring 160 causing downward movement of the spring and corresponding release of the pusher tube 134. This action causes distal movement of pusher tube 134 and clip pusher 78' with corresponding distal engagement of nose 80' with the next clip 22' thereby positioning the clip into the slots 54', 56' of jaws 24'.

Once clip 22' is positioned within jaws 24' of jaw blade 26' squeezing handle 18' proximally toward hand grip 20' causes distal and pivotal movement of channel links 116, 118, resulting in distal movement of channel tube 124 and corresponding distal movement of crimping channel 32'. This action causes channel bracket 38 together with crimping channel 32' to engage and squeeze the jaw members 24' of jaw blade 26' thereby crimping the clip 22' positioned therebetween. At the same time, the proximal movement of pusher tube 134 resets clip pusher 78' to a position just proximal of the next clip in readiness for the next clipping operation. Reentry of the tab 162 of pusher release spring 160 into slot 161 of pusher tube 134 retains the pusher 78' in position behind the next clip 22'.

Figure 31:
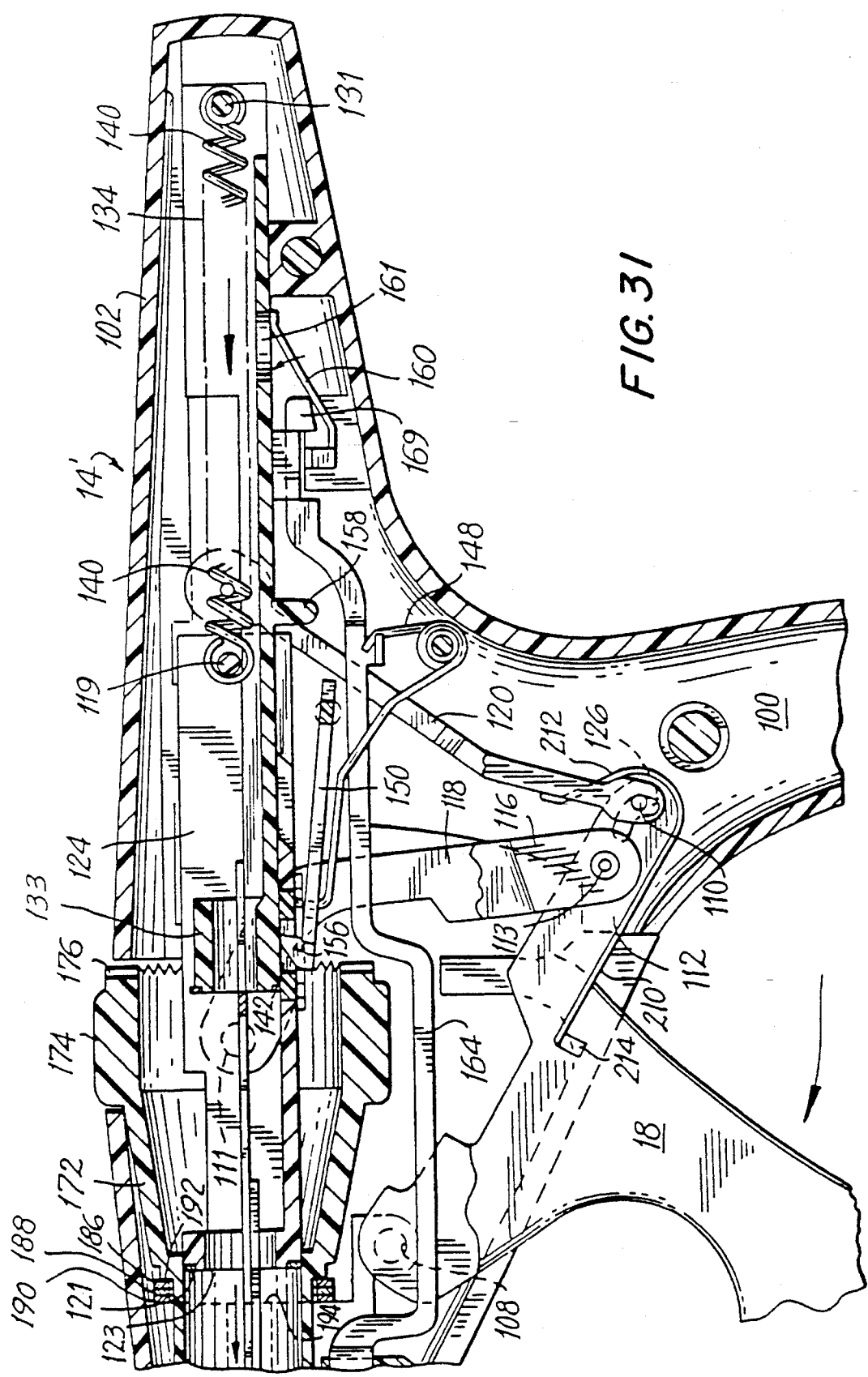
FIG. 31 is an elevational cross-sectional view of the handle of the apparatus of FIG. 16 illustrating the channel tube in the normal "at rest" position and the pusher tube in the loaded position corresponding to the position of the clip pusher in the proximal position about to push the next clip distally into the jaws.
Figure 32:
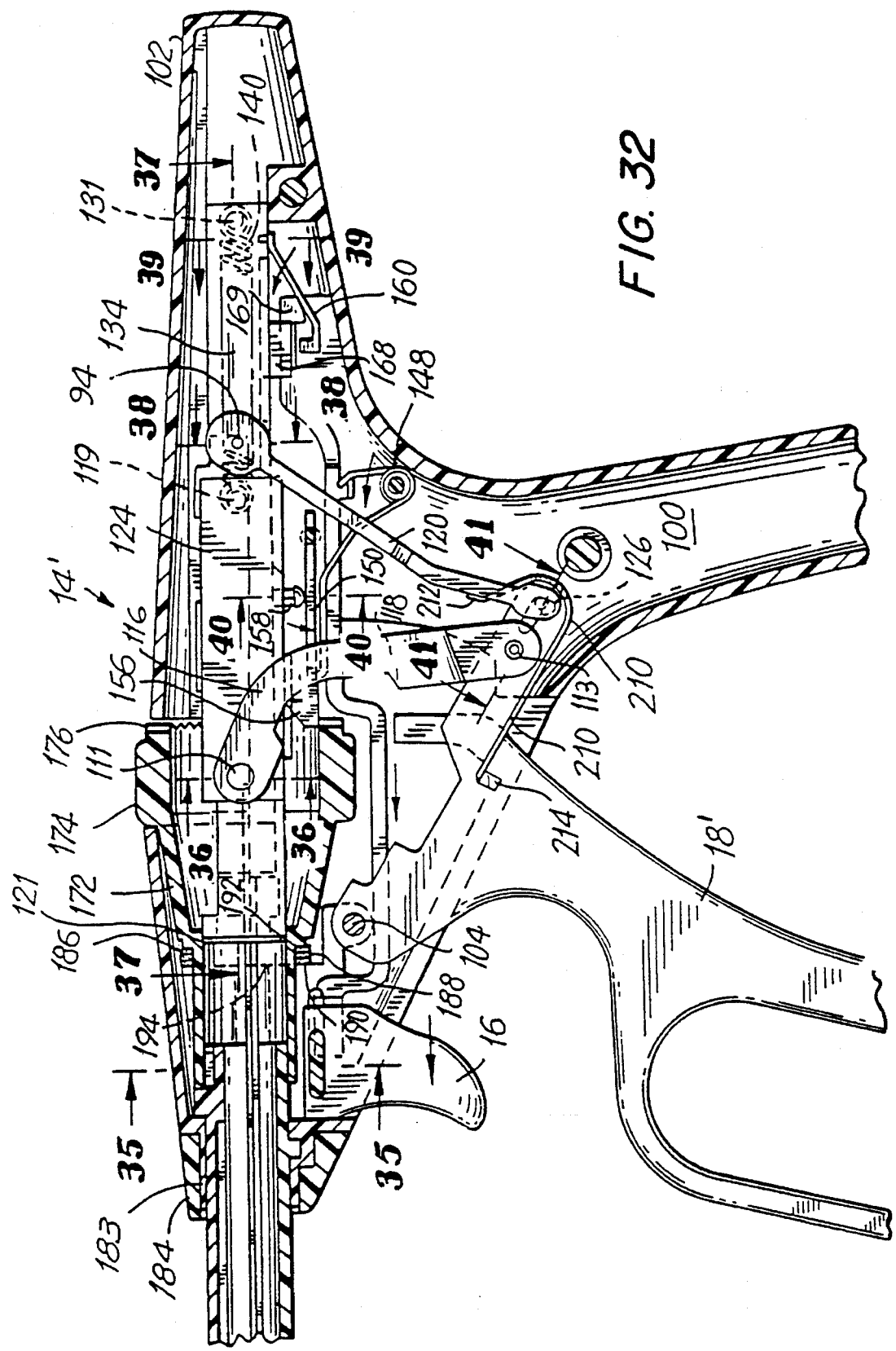
FIG. 32 is an elevational cross-sectional view of the handle of the apparatus of FIG. 16 with the pusher tube extended to its distal-most position corresponding to the position of the clip pusher after positioning a clip between the jaws, and the channel tube in its proximal position corresponding to the position of the clip pusher after positioning a clip between the jaws, and the channel tube in its proximal position corresponding to open jaws at the distal-most position of the endoscopic section.
Figure 33:
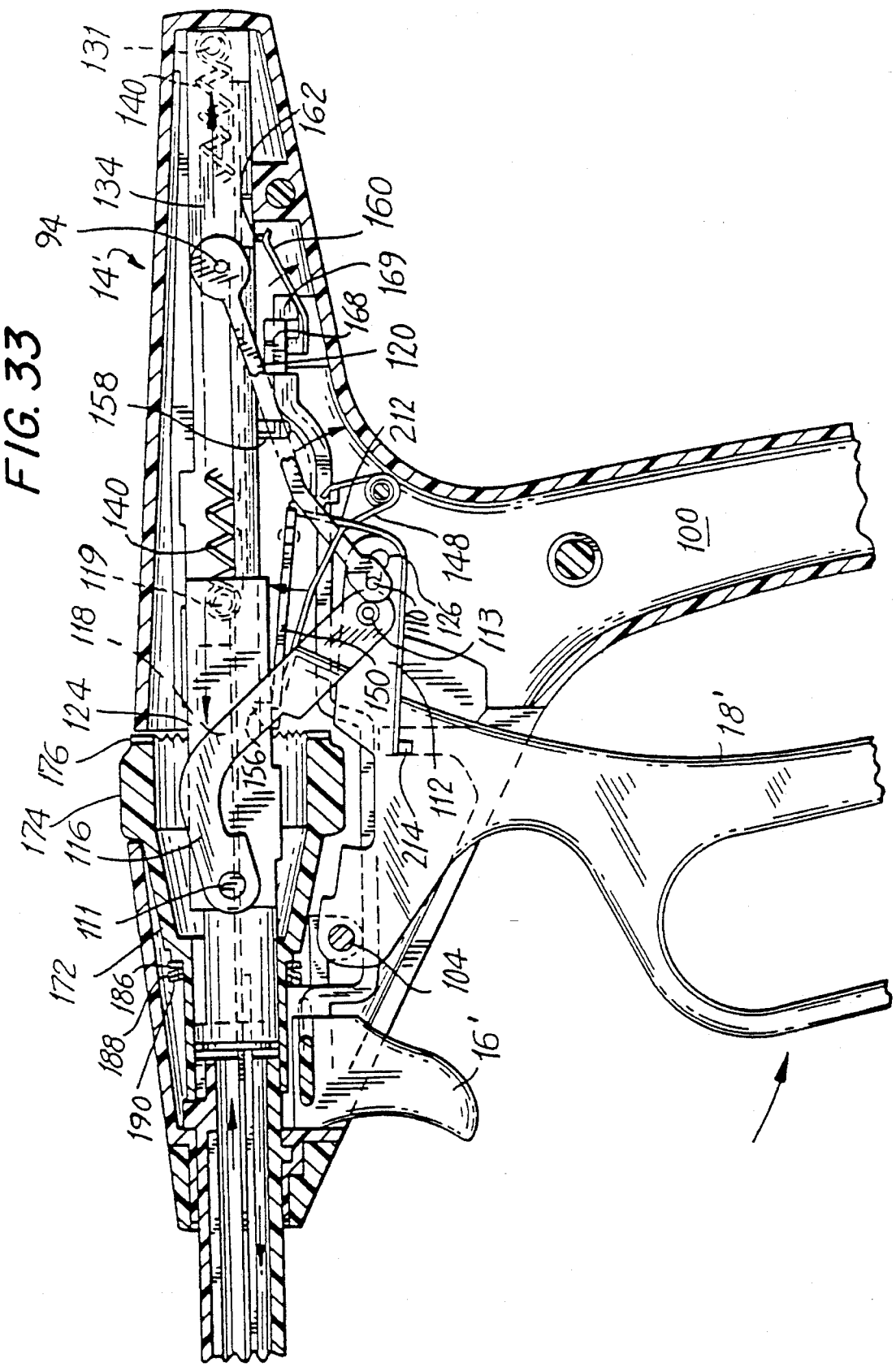
FIG. 33 is an elevational cross-sectional view of the handle section of the apparatus of FIG. 16 illustrating the pusher tube in its proximal position corresponding to the clip pusher in position behind the next clip to be advanced and the channel tube in its distal-most position after having closed the jaws.

Referring further to FIG. 18 in conjunction with FIG. 17, the feature relating to the rotatable endoscopic section will be described. Rotating collar 170 is constructed of the same material as the handle, i.e. preferably a polycarbonate material such as LEXAN brand material. This collar 170 includes a distal cylindrical nose section 172 and a proximal barrel section 174. The proximal face of the barrel section 174 includes a plurality of proximally extending teeth 176 positioned circumferentially about the proximal face of the barrel section and the cylindrical nose section includes an inwardly extending rib 178 at the distal end. In the assembled condition, the cylindrical nose section rests within the cylindrical distal opening 182 of the distal end of the handle and nose piece 184 is fitted over the distal cylindrical end 183 of the handle as shown in FIGS. 31–33. Bearing washer 186 and spring washers 188, 190 are positioned between shoulder 192 of collar 170 and shoulder 194 formed in the handle body to bias the rotatable collar in the proximal direction causing tooth 180 on the handle body to engage the teeth 176 of the collar 170 to thereby fix the rotatable orientation of the collar. When the surgeon desires to change the angular orientation of the endoscopic section, the collar 170 is merely pushed distally to disengage tooth 180 to free the collar and permit rotation relative to the handle body. Such rotation of the collar is clearly permitted by the fact that the cylindrical nose section of the collar is fit snugly within the corresponding cylindrical distal section 182 of the handle. Except when the tooth 180 of the handle body is engaged with teeth 176 of collar 170, the collar is otherwise free to rotate within the handle.

Referring now to FIG. 17 in conjunction with FIGS. 16 and 18, the distal cylindrical section 172 of collar 170 includes a distal cylindrical opening dimensioned to receive the endoscopic cartridge formed of upper half 15*a* and lower half 16', with distally positioned tooth 178 of collar 170 positioned within longitudinally extending groove 15a' of upper cartridge half 15a to cause the cartridge to rotate with the collar 170. Similarly, the proximal legs 90' of clip pusher bar 78' are permitted to rotate within the distal end portion 133 of pusher tube 134 and the proximal legs 92' of the crimping channel 32' are permitted to rotate within the distal end portion 123 of channel tube 124. Thus, the entire endoscopic section may be selectively rotated by the surgeon by simply pushing collar 170 in the distal direction sufficient to disengage tooth 180 on the handle body and by rotating the collar 170 until the endoscopic section reaches the desired angular orientation. Thereafter, by merely releasing the collar the bias of spring washers 190, 188, causes the collar to move proximally, such that tooth 180 on the handle body engages the appropriate teeth 176 on the collar 170 to lock the position of the collar and the endoscopic section. This feature represents a significant advance in endoscopic surgery when it is fully appreciated that the orientation of human tissue or arteries to be clamped vary widely and that selectivity of orientation of the clip is a necessity. Without the above-described feature, the entire apparatus must otherwise be rotated until the proper orientation of the endoscopic section is reached. Such rotation of the entire apparatus during a delicate surgical operation would be prohibitive.

Figure 27:
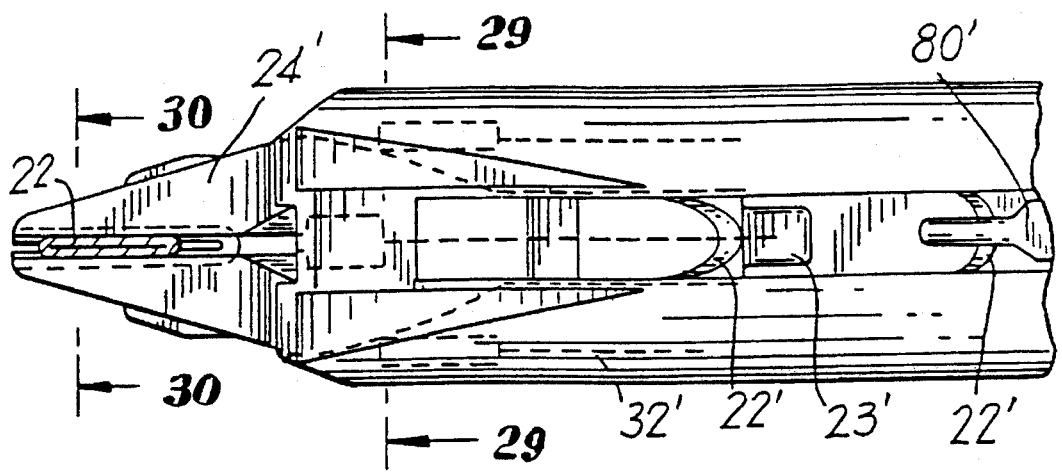
FIG. 27 is a plan view from above of the distal portion of the endoscopic section illustrating a clip positioned within the jaws after clamping is completed about an artery.
Figure 28:
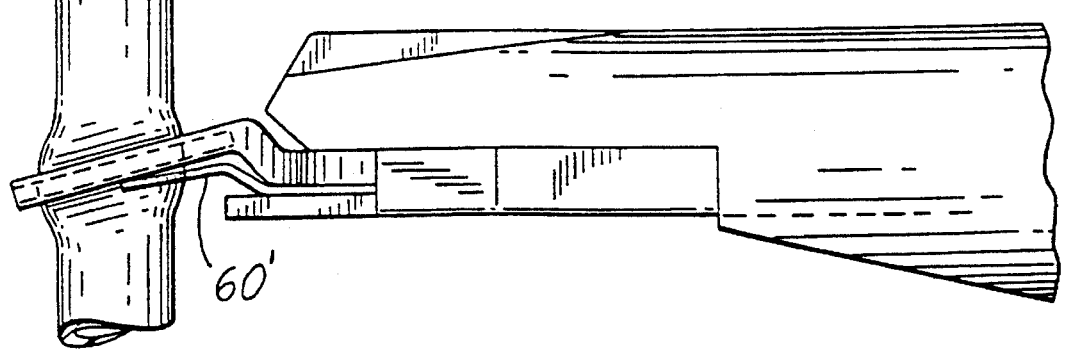
FIG. 28 is a side view thereof.

Referring now to FIGS. 27, 28, 29 and 30, the jaws of the clamping section of the apparatus are illustrated. FIG. 27 illustrates the jaws 24' of the apparatus in position after having applied a clip 22' about an artery 98' or other blood vessel to stop the blood flow as illustrated graphically in FIG. 30. As shown in FIG. 30, the jaw members 24' include longitudinally extending grooves 54', 56' which receive clip 22' as the clip is advanced distally by pusher bar 78'. It can be seen that at the time the jaw members 24' are clamped together, the nose 80' of pusher bar 78' has been withdrawn proximally to a position proximal of the next clip 22' and is not permitted to advance in the distal direction until the surgeon pulls pusher release button 16' in the proximal direction to release the clip pusher mechanism described previously. Tab 23' prevents the next clip from moving proximally with the pusher bar when the pusher bar returns to a position proximal of the next clip for the sequence. Also, prior to release of the pusher bar for distal movement, fingers 21' upstanding from track 66' prevent distal movement of the next clip preventing the clip from falling out through the jaws. In addition, it is significant to note that once the jaw members 24' are released from their clamped condition shown in FIG. 27, by release of handle 18', clamping of the jaw members 24' may not be repeated until the pusher release button 16' has been depressed to deliver the next clip between the jaws 24'. Such clamping action is prevented by the position of tongue 156 within the aperture of plate 146 in the bottom wall of channel tube 124 under the upward bias of spring 148. This position prevents distal movement of the channel tube 124 until the tongue 156 is released from the aperture of plate 146 by engagement of downwardly extending finger 158 of pusher tube 134 with latch plate 150 when pusher tube 134 is caused to advance distally by releasing pusher release button 16'.

The release action on tongue 156 is shown more clearly in FIG. 32 which illustrates the handle with the pusher tube 134 in the distal-most position after pusher release button 16' has been depressed to advance the next clip into the jaw members 24' of jaw blade 26'. It can be seen clearly in FIG. 32 that finger 158 has engaged latch plate 150 pivoting the latch plate downwardly in the counter clockwise direction against the upward bias of latch spring 148. It will similarly be appreciated that the proximal movement of pusher tube 134 during the squeezing action of handle 18' and jaw members 24' will continue until the tab 162 of the upwardly biased pusher release spring 160 engages the slot in the bottom wall of the proximal section of pusher tube 134 thereby causing the pusher tube to be locked in position corresponding to the nose 80' of pusher bar 78' being positioned just proximal of the next clip 22' for the next clip advancing step as described hereinabove. It can be appreciated readily that this safety feature avoids the possibility of squeezing the jaw members 24' about an artery or other tissue with no clip positioned therebetween. Thus, the only time in the sequence of operation that the jaws can be squeezed is after the advancement of a clip 22' therebetween.

Referring now to FIGS. 19–26, the inner mechanism and function of the distal portion of the endoscopic section are illustrated. In FIG. 19 a plan view from above, is shown of the distal portion of the endoscopic section, illustrating the jaw members 24' and the nose 80' of pusher bar 78' in position to advance the clip 22' into the jaw members. At this time, the row of clips 22' are advanced to their distal-most positions under bias action of clip feed spring 72' between anchor pin 74' on cover plate pin anchor tab 66a and pin 71' on clip follower 68' shown in FIG. 17. FIG. 20 is a cross-sectional view taken along lines 20—20 of FIG. 19 illustrating the clip 22' and the nose 80' of pusher bar 78' in position just proximally thereof. The view of the nose 80' of pusher bar 78' shown in dotted lines is intended to illustrate the proximal-most position of the nose 80' of pusher bar 78' as represented by the last portion of the squeezing motion of handle 18' toward hand grip 20' thus establishing with certainty, that the nose 80' of clip pusher 78' is in fact positioned proximally of the next clip 22' after the handle 18' is released and the nose 80' of pusher bar 78' is permitted to move distally a small distance as shown behind clip 22' as represented by relaxation of the combined tolerance build-up of the components interacting with each other. Escapement means in the form of upstanding tabs 21' in cover plate 66' prevent the next clip 22' from distal movement before it has been advanced distally by the pusher bar 78'. Arch 21a assists proper orientation of the clip entering the jaws. Tab 23' prevents proximal movement of clip 22' once it has been advanced distally by clip follower 68' and clip feed spring 72', i.e. the proximal return movement of nose 80' does not move clip proximally (by friction) along with the nose.

FIG. 20a illustrates still another significant feature which prevents further distal advancement of the clip pusher 78' after the last clip 22' has been advanced distally into the jaws 24' and clamped about an artery. In particular, the proximal portion of clip follower 68' includes upstanding tab 67' which is positioned and dimensioned to engage bridge 88' on upper cartridge half 15a when clip follower 68' assumes the distal-most position shown in FIG. 20a under bias of spring 72'. This position is assumed by clip follower 68' after the last clip has been advanced distally into the jaws 24'. Thus, the engagement of upstanding tab 67' with bridge 88' prevents further distal movement of the clip follower at this stage. Furthermore, as shown in FIG. 20a, the distal position of clip follower 68' results in slot 65' now assuming its distal-most position such that nose 80' of clip pusher bar 78' may drop into slot 65' thus preventing further distal movement of the pusher bar 78' after the last clip has been spent. This is a further safety feature in that the apparatus is inactivated after the last clip is spent, thus avoiding the possibility of the surgeon clamping the jaws 24' about an artery with no clip in position. FIG. 20b is a cross-sectional view taken along lines 20b—20b of FIG. 20 illustrating the clip follower 68' and the clip cover plate 66' in the position shown in FIG. 20*a*.

Referring now to FIG. 21, a plan view from above similar to FIG. 19 is shown of the distal portion of the endoscopic section with clip 22' shown in FIG. 20 now advanced distally to a position within the jaws 24' by nose 80' of clip pusher 78'. FIG. 22 is a cross-sectional view taken along lines 22—22 of FIG. 21 illustrating the clip 22' and clip pusher bar 78' in the distally advanced position after advancing clip 22' into the jaws 24'.

Referring now to FIG. 23 there is shown a cross-sectional view taken along lines 23—23 of FIG. 21 which illustrates a safety locking feature. This safety locking feature prevents use of the present endoscopic clip applier with a cannula of incorrect size. In particular, it can be seen that the safety device 202 includes housing 204 having locking collar 206 retained in place in the housing by interference fit or adhesive. A plurality of locking fingers 208 are positioned circumfer-entially about the collar and are constructed of a resilient material which causes their arcuate bent end portions 210 to become locked into position within a circumferential groove 212 formed in the cartridge halves 15*a* and 17. This longitudinal movement of the locking collar 206 relative to the endoscopic section is prevented unless the bent end portions 208*c* of fingers 208 are lifted upwardly out of the groove 212. In endoscopic surgical procedures, a cannula in the form of a trocar guide tube is generally positioned within the body wall and extends into the peritoneal cavity which has been insufflated by a gas to protect the body organs. The trocar guide tube normally includes a valve device to maintain the gas under pressure and camming devices of appropriate size and shape to disengage fingers 208 from groove 212. Thus, when the endoscopic section of an instrument is inserted into the trocar guide tube it is necessary to use the correct size guide tube for the endoscopic device. The endoscopic section preferably contains a small quantity of silicone grease with the housing to prevent leakage of gas through the housing.

Referring to FIG. 23, an exemplary part of an entry portion 209 of a trocar guide tube is shown with remaining parts broken away for illustrative purposes. Entry wall 209 of the trocar guide tube is shown with a plurality of camming members 211 configured, dimensioned and positioned to simultaneously lift fingers 206 out of groove 212 to release the safety locking device 202 and permit it to slide proximally along the endoscopic section. Only one camming member 211 is shown for convenience.

When the endoscopic section 14 is inserted into the trocar guide tube, if the diameter of the guide tube is excessive, distal movement of the endoscopic section will be prevented by the engagement with collar 202. If the diameter of the trocar guide tube is too small, distal movement of the endoscopic section will be prevented by engagement of the fingers 208 with the guide tube. However, when the trocar guide tube is the correct size and shape, the fingers 206 will be lifted simultaneously out of groove 212 by camming members 211 and collar 202 will readily be permitted to slide in the proximal direction along the endoscopic cartridge thereby permitting insertion of the endoscopic section into the guide tube without loss of gas from the peritoneal cavity. Other appropriate seals are included in the trocar guide tube. The safety locking collar 202 shown is similar to the safety locking collar disclosed in commonly assigned U.S. Pat. No. 5,129,885, the disclosure of which is incorporated by reference herein and made a part of this disclosure.

FIG. 24 is a cross-sectional view taken along lines 24—24 of FIG. 21, illustrating the crimping channel 32', the tissue stop 64', clip 22', pusher bar 78' and jaws 24', and cover plate (or clip track) 66'.

Figure 25:
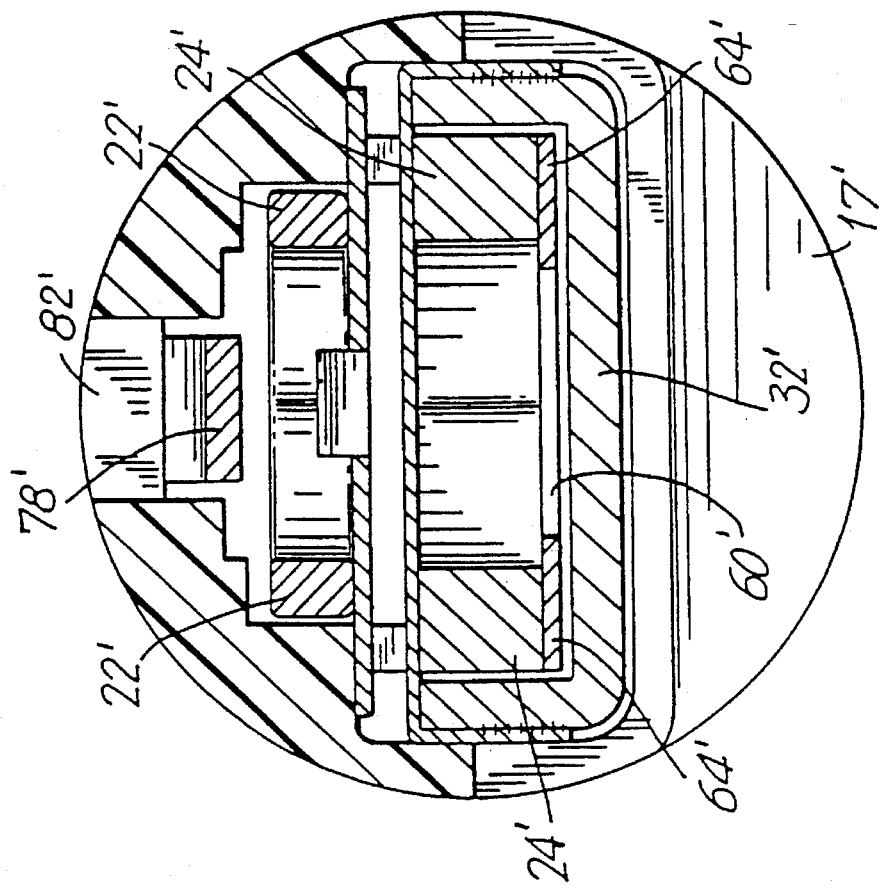
FIG. 25 is a cross-sectional view taken along lines 25—25 of FIG. 21.
Figure 26:
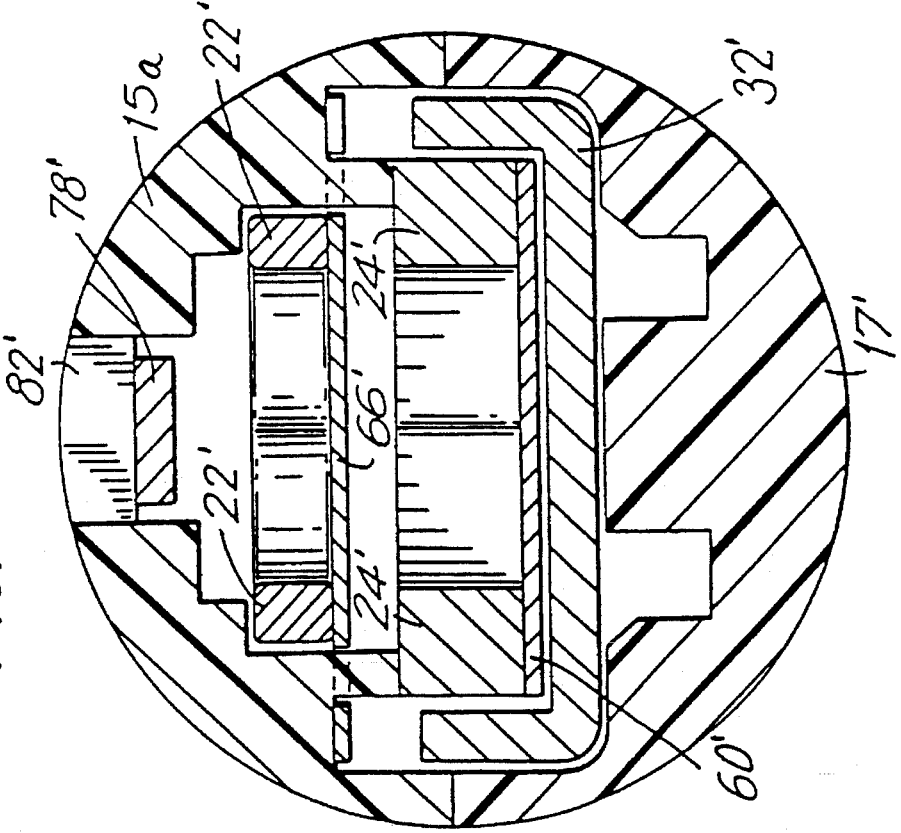
FIG. 26 is a cross-sectional view taken along lines 26—26 of FIG. 21.

FIG. 25 is a similar cross-sectional view taken along lines 25—25 of FIG. 21 illustrating the clip advancing components. FIG. 26 is a cross-sectional view similar to FIG. 25 illustrating the clip advancing mechanism distal of the cross-section shown in FIG. 25.

Referring now to FIGS. 31–34, the inner clip advancing and jaw squeezing mechanism is shown in various stages of the operation. FIG. 31 is an elevational cross-sectional view of the handle 18 of the apparatus, illustrating the pusher tube 134 in the proximal-most position corresponding to the position of the pusher bar 78' shown in FIG. 20, i.e. with the nose 80' just proximal of the next clip 22' in readiness to activate the clip distally into the jaws 24'. Additionally, with pusher tube in the proximal position, downwardly extending finger 158 has moved out of engagement with latch 150 thereby permitting tongue 156 to enter the aperture of channel latch plate 146 thus preventing any distal movement of channel tube 124. This condition locks handle 18' in the distal position whereby squeezing the handle toward hand grip 20' is prevented.

Referring now to FIG. 32, there is shown a cross-sectional view of the handle 18' of the apparatus with the pusher tube in the distal-most position corresponding to the position of pusher bar 78' as shown in FIG. 22, i.e. with the clip 22' advanced distally into the jaws 24' of jaw blade 26'. As can be seen further in FIG. 32, the distal position of pusher tube 134 has now resulted in release of tongue 156 of latch plate 150 from the aperture of channel latch plate 146 in the bottom wall of channel tube 124 thereby permitting advancement of channel tube 124 and crimping channel 32' distally to squeeze jaws 24' in conjunction with channel bracket 38'.

Referring now to FIG. 33, a cross-sectional view of the handle 18' is shown after the crimping action has taken place on clip 22' positioned within jaws 24' shown in FIGS. 31 and 22. The position of the components shown in FIG. 33 corresponds to the position of the jaws shown in FIGS. 27–30, i.e., in the clamped position about clip 22'. In the cross-section shown in FIG. 33, the pusher tube 134 in the proximal-most position and the channel tube is in the distal-most position such that crimping channel 32' and channel bracket 40' are in the distal-most position shown in FIGS. 27–30.

Figure 34:
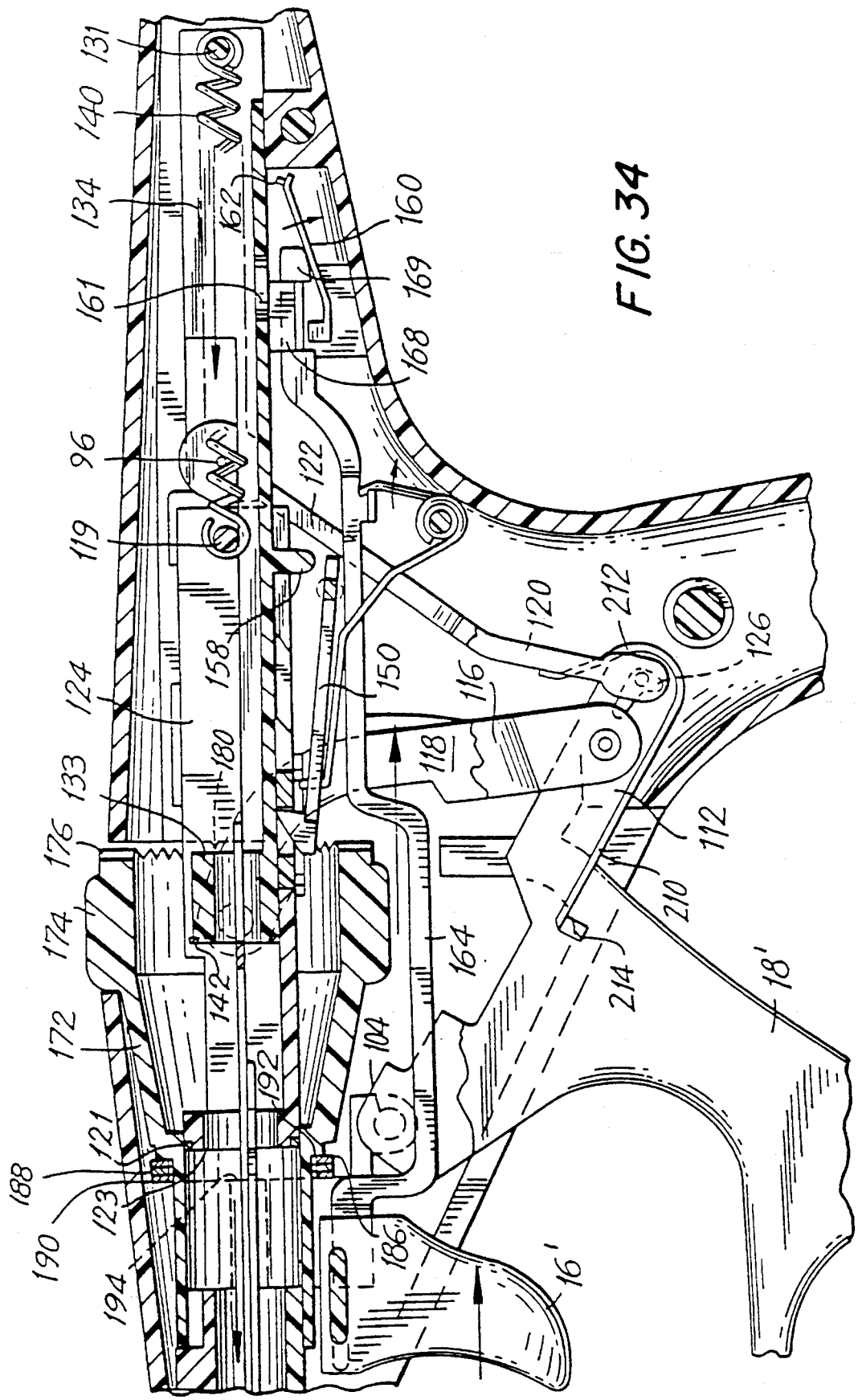
FIG. 34 is an elevational cross-sectional view of the handle of FIG. 16 illustrating the channel tube in locked position after the last clip has been pushed into the jaws of the endoscopic section and the pusher bar has engaged a distal slot in the clip follower, locking the pusher tube in the position shown.
Figure 39:
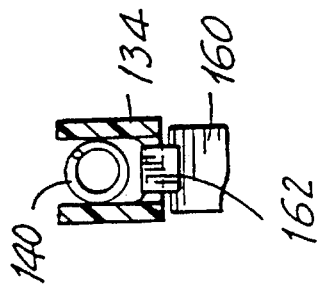
FIG. 39 is a cross-sectional view taken along lines 39—39 of FIG. 32, illustrating the pusher tube and the mainspring.
Figure 40:
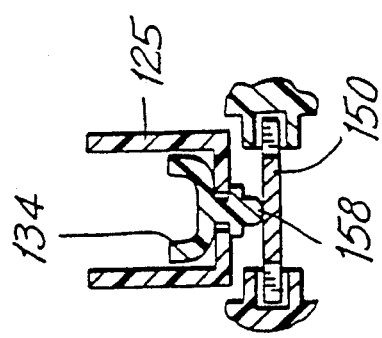
FIG. 40 is a cross-sectional view taken along lines 40—40 of FIG. 32 illustrating release of the channel tube latch plate by the pusher tube.
Figure 41:
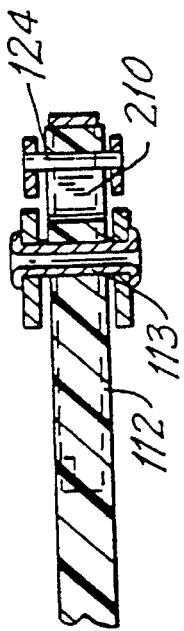
FIG. 41 is a cross-sectional view taken along lines 41—41 of FIG. 32 illustrating the lost motion spring which permits partial clamping of the surgical clips.
Figure 38:
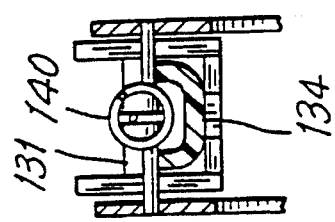
FIG. 38 is a cross-sectional view taken along lines 38—38 of FIG. 32, illustrating the pusher tube and the pusher tube link pin.

Referring to FIG. 34 a cross-sectional view of the handle 18' is shown after the last clip 22' has been spent, i.e. corresponding to the position of the clip follower 68' shown in FIG. 20*a*. As noted hereinabove, the clip follower 68' of the endoscopic section is prevented from moving further distally by interaction with bridge 88' formed in upper cartridge half section 15*a*. Additionally as noted, it can be seen in FIG. 20*a* that clip follower 68' defines slot 65' at the distal portion which is bounded on the distal end by a bridge 63' which is positioned to engage the nose 80' of pusher bar 78' when clip follower 68' has advanced to the distal-most position shown in FIG. 20*a*, i.e. after the last clip has been spent. In this position, the clip follower is now sufficiently distal to engage the nose 80' of clip pusher bar 78' which is biased downwardly by the configuration of pusher bar 78' and by the resilient properties of the material from which the pusher bar is fabricated, i.e. stainless steel. This engagement with bridge 63' prevents further distal movement of clip pusher bar 78' and correspondingly of pusher tube 134. By preventing pusher tube 134 from distal movement with channel tube 124 locked in its proximal position by tongue 156 of latch plate 150, further squeezing action of handle 18' toward hand grip 20' is also prevented. This locking action correspondingly prevents distal movement of crimping channel 32'. As shown in FIG. 34, pusher release button is depressed but full distal movement of pusher tube 134 is prevented by the engagement of nose 80' of pusher bar 78' with bridge 63' of clip follower. Only a small distal movement is permitted as seen by the position of slot 161 in pusher tube 134 relative to the position of pusher release spring 160. This locked position of pusher tube 134 also serves to prevent downwardly depending finger 158 of pusher tube 134 from distal movement sufficient to release tongue 156 of latch plate 150 from channel tube 124 as shown. Thus, the crimping mechanism is inactivated for safety purposes.

This feature is extremely significant in disabling the apparatus from squeezing jaws 24' of the jaw blade 26' on an artery alone, i.e. with no clip positioned therebetween. Further, all movement of the clip advance mechanism is now prevented after the last clip has been spent. At this stage, the entire instrument is considered disposable and may be disposed of in accordance with correct approved disposal procedures.

Referring once again to FIG. 18 in conjunction with FIGS. 31–34, the lost motion spring 210 is shown having transverse arms 212 and tab 214. Spring 210 provides bias force on pusher links 120, 122 such that squeezing action on handle 18' maximizes proximal movement of pusher tube 134. Thus, partially closing the jaws 24' of jaw blade 26' will cause pusher tube 134 to move sufficiently proximal to make certain that pusher bar 78' has moved proximally of the next clip 22'. Without such movement it may be possible for the surgeon to squeeze the jaws, not fully appreciating that the pusher bar 78' has not moved to a position proximal of the next clip 22'. This proximal movement of the pusher bar transmission is thus assisted by lost motion spring 210 which maximizes the repositioning movement of the pusher bar 78' behind the next clip whether the jaws are squeezed fully or partially. In particular, the proximal bias provided by spring 210 on pusher links 120, 122 maximizes the movement of pusher tube 134 in relation to the movement of handle 18' by maintaining pusher links 120, 122 in their proximal-most positions prior to squeezing the handle 18'. This maximum proximal movement of pusher links 120, 122 in turn results in proximal movement of pusher tube sufficient to engage tongue 162 of release spring 160 thus making certain that pusher bar 178 is repositioned sufficiently proximally to advance the next clip 22' into the jaw members 24'.

What is claimed is:

1. A surgical clip advancing system which comprises:
   an elongated clip carrier defining a longitudinal axis and a clip-supporting face;
   a plurality of surgical clips in contact with the clip-supporting face of the elongated carrier;
   an elongated pusher bar movably mounted with respect to the elongated carrier, the pusher bar having a distal end and a proximal end and including a nose at its distal end, the nose having a pair of members extending substantially transverse to the longitudinal axis, each substantially transverse member including a distally facing clip contacting surface and an angular cam surface proximal to the clip contacting surface.

2. The system of claim 1, wherein the distal end of the pusher bar is angled with respect to the longitudinal axis.

3. The system of claim 1, wherein the elongated clip carrier is an elongated channel having a pair of side walls between which the surgical clips are slidably guided.

4. The system of claim 1, further comprising a pusher and a biasing spring positioned proximal of the plurality of surgical clips, wherein the pusher and biasing spring distally bias the plurality of surgical clips along the clip carrier.

5. The system of claim 1, further comprising at least one finger upstanding from the clip carrier, wherein the at least one finger prevents distal movement of the surgical clips.

6. The system of claim 1, further comprising a tab extending from the clip carrier, wherein the tab prevents proximal movement of a distal-most surgical clip in contact with the clip supporting face of the clip carrier.

7. The system of claim 1, wherein the plurality of surgical clips are U-shaped and are aligned in an array in contact with the clip-supporting face of the clip carrier.

\* \* \* \* \*